(12) United States Patent
Weber et al.

(10) Patent No.: US 7,638,306 B2
(45) Date of Patent: Dec. 29, 2009

(54) PROCESS OF INCREASING CELLULAR PRODUCTION OF BIOLOGICALLY ACTIVE COMPOUNDS

(75) Inventors: J. Mark Weber, Chicago, IL (US); Andrew R. Reeves, Chicago, IL (US); Igor A. Brikun, Forest Park, IL (US); William Henry Cernota, Chicago, IL (US)

(73) Assignee: Fermalogic, Inc., Chicago, IL (US)

( * ) Notice: Subject to any disclaimer, the term of this patent is extended or adjusted under 35 U.S.C. 154(b) by 789 days.

(21) Appl. No.: 10/637,159

(22) Filed: Aug. 8, 2003

(65) Prior Publication Data

US 2006/0234958 A1 Oct. 19, 2006

(51) Int. Cl.
C12P 19/62 (2006.01)
C12N 9/00 (2006.01)
C12N 9/10 (2006.01)
C12N 1/20 (2006.01)

(52) U.S. Cl. .................. 435/76; 435/183; 435/193; 435/252.3

(58) Field of Classification Search ............. 435/76, 435/6, 183, 193, 252.3, 252.35; 514/28, 514/84, 29, 183, 294
See application file for complete search history.

(56) References Cited

OTHER PUBLICATIONS

Vrijbloed et al. Insertional inactivation of methylmalonyl coenzyme A (CoA) mutase and isobutyryl-CoA mutase genes in *Streptomyces cinnamonensis*: influence on polyketide antibiotic biosynthesis, J Bacteriol. Sep. 1999; 181(18): 5600-5.*
Katz et al. Novel macrolides through genetic engineering, Med Res Rev. Nov. 1999; 19(6): 543-58. Review.*
Whisstock et al. Quaterly Reviews of Biophysics, 2003, "Prediction of protein function from protein sequence and structure", 36(3): 307-340.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
T. E. Weber, A. P. Schinckel, K. L. Houseknecht and B. T. Richert. 2001. Evaluation of conjugated linoleic acid and dietary antibiotics as growth promotants in weanling pigs. J Anim Sci. 79:2542-2549.
Aparicio, JF, Cafrey P, Gil JA, Zotchev SB. Polyene antibiotic biosynthesis gene clusters. Appl Microbiol Biotechnol. May 2003;61(3):179-88. Epub 2002 Dec 18.
Aparicio JF, Molnar I, Schwecke T, Konig A, Haydock SF, Khaw LE, Staunton J, Leadleyγ PF. Organization of the biosynthetic gene cluster for rapamycin in Streptomyces hygroscopicus: analysis of the enzymatic domains in the modular polyketide synthase. Gene. Feb 22, 1996;169(1):9-16.
Bibb MJ, White J, Ward JM, Janssen GR. The mRNA for the 23S rRNA methylase encoded by the ermE gene of Saccharopolyspora erythraea is translated in the absence of a conventional ribosome-binding site. Mol Microbiol. Nov. 1994;14(3):533-45.
Bircha, Leiser A, Robinson JA. Cloning, sequencing, and expression of the gene encoding methylmalonylcoenzyme A 20 mutase from Streptomyces cinnamonensis. J Bacteriol. Jun. 1993;175(11):3511-9.
Dayem LC, Carney JR, SantI DV, Pfeifer BA, Khosla C, Kealey JT. Metabolic engineering of a methylmalonyl-CoA mutase-epimerase pathway for complex polyketide biosynthesis in Escherichia coli. Biochemistry. Apr. 2002 23;41(16):5193-201.
Donadio S, Stayer MJ, Katz L. Erythromycin production in Saccharopolyspora erythraea does not require a functional propionyl-CoA carboxylase. Mol Microbiol. mar. 1996;19(5):977-84.
Dotzlaf JE, Metzger LS, Fogelsong MA. Incorporation of amino acid-derived carbon into tylactone by Streptomyces fradiae GS 14. Antimicrob Agents Chemother. Feb. 1984;25(2):216-20.
Fleischmann RD, Adams MD, White 0, Clayton RA, Kirkness EF, Kerlavage AR, Bult CJ, Tomb JF, Dougherty BA, Merrick JM, et al. Whole-genome random sequencing and assembly of Haemophilus influenzae Rd. Science. Jul 28, 1995;269(5223):496-512.
Gerth K, Bedorf N, Iirschik H, Hofle G, Reichenbach H. The soraphens: a family of novel antifungal compounds from Sorangium cellulosum (Myxobacteria). I. Soraphen Al alpha: fermentation, isolation, biological properties. J Antibiot (Tokyo). Jan. 1994;47(1):23-31.
Gil JA. Campelo-Diez AB. Candicidin biosynthesis in Streptomyces griseus. Appl Microbiol Biotechnol. 2003 Feb;60(6):633-42. Epub Dec. 18, 2002. Review.
Goryshin IY, Reznikoff WS. Tn5 in vitro transposition. J. Biol. Chem. 1998 273: 7367-74.
Haydock SF, Aparicio JP, Molnar I, Schwecke T, Khaw LE, Konig A, Marsden AF, Galloway IS, Staunton J., Leadlay PF. Divergent sequence motifs correlated with the substrate specificity of (methyl)malonylCoA:acyl carrier protein transacylase domains in modular polyketide synthases. FEBS Lett. Oct 30. 1995;374(2):246-8.
Hsieh YJ, Kolattukudy PE. Inhibition of erythromycin synthesis by disruption of malonyl-coenzyme a decarboxylase gene eryM in Saccharopolyspora erythraea. J Bacteriol. Feb. 1994;176(3):714-24.
Hunaiti AA, Kolattukudy PE. Source of methylmalonyl-coenzyme a for erythromycin synthesis: methylmalony-coenzyme a mutase from Streptomyces elythreus. Antimicrob Agents Chemother. Feb. 1984;25 (2):173-8.
Hu Z, Bao K., Zhou X, Zhou Q, Hopwood Da, Kieser T. Deng Z. Repeated polyketide synthase modules involved in the biosynthesis of a heptaene macrolide by Streptomyces sp. Fr-008. Mol Microbiol. 1994 Oct;14 (1):163-72.
Ikeda H, Nonomiya T, Usami M., Ohta T., Omura S. Organization of the biosynthetic gene cluster for the polyketide anthelmintic macrolide avermectin in Streptomyces avermitilis. Proc Natl Acad Sci U S a. 1999 Aug 17;96 (17):9509-14.

(Continued)

Primary Examiner—Richard Hutson
Assistant Examiner—Iqbal H Chowdhury
(74) Attorney, Agent, or Firm—Quarles & Brady LLP

(57) ABSTRACT

A process of increasing the cellular production of biologically active compounds is provided. The process is particularly useful for increasing antibiotic production by bacterial cells. The process includes the step of inhibiting the activity of methylmalonyl-CoA mutase.

5 Claims, 7 Drawing Sheets

OTHER PUBLICATIONS

Kellermeyer Rw, Allen Shg, Stjernholm R, and Wood HG. Methylmalonyl isomerase. IV. Purification and properties of the enzyme from Propionibacteria. J. Biol. Chem. 1964 239:2562-2569.

Liu H, Reynolds Ka. Role of crotonyl coenzyme a reductase in determining the ratio of polyketides monensin a and monensin B produced by Streptomyces cinnamonensis. J Bacteriol. Nov. 1999;181(21):6806-13.

Marsh EN, McKie N, Davis NK, Leadlay PF. Cloning and structural characterization of the genes coding for adenosylcobalamin-45 dependent methylmalonyl-CoA mutase from Propionibacterium shermanii. Biochem J. Jun 1, 1989;260(2):345-52.

Miller ES. Cloning vectors, mutagenesis, and gene disruption (ermR) for the erythromycin-producing bacterium Aeromicrobium erythreum. Appl Environ Microbiol. Sep. 1991;57(9):2758-61.

Mochizuki S. Hiratsu K, Suwa M. Ishii T, Sugino F, Yamada K. Kinashi H. The large linear plasmid pSLA2- L of Streptomyces rochei has an unusually condensed gene organization for secondary metabolism. Mol Microbiol. Jun. 2003;48(6):1501-10.

Molnar I, Aparicio JF, Haydock SF, Khaw LE, Schweckee T, Konig A, Staunton J. Leadlay PF. Organisation of the biosynthetic gene cluster for rapamycin in Streptomyces hygroscopicus: analysis of genes flanking the polyketide synthase. Gene. Feb 22, 1996;169(1):1-7.

OH SS, Chater KF. Denaturation of circular or linear DNA facilitates targeted integrative transformation of Streptomyces coelicolor A3(2): possible relevance to other 20 organisms. J Bacteriol. Jan. 1997;179(1):122-7.

Omura S, Tsuzki K, Tanaka Y, Sakakibara H, Aizawa M, Lukacs G. Valine as a precursor of n-butyrate unit in the biosynthesis of macrolide aglycone. J Antibiot (Tokyo). May 1983;36(5):614-6.

Omura S, Taki A, Matsuda K, Tanaka Y. Ammonium ions suppress the amino acid metabolism involved in the biosynthesis of protylonolide in a mutant of *Streptomyces fradiae*. J Antibiot (Tokyo). 1984 Nov;37(11):1362-9.

Omura S, Takeshima H. Nakagawa A. Miyazawa J, Piriou F, Lukacs G. Studies on the biosynthesis of 16- membered macrolide antibiotics using carbon-13 nuclear magnetic resonance spectroscopy. Biochemistry. Jun. 28, 1977;16(13):2860-6.

Paulus TJ, Tuan JS, Luebke VE, Maine GT, Dewitt JP, Katz L. Mutation and cloning of etyG, the structural gene for erythromycin 0-methyltransferase from Saccharopolyspora erythraea, and expression of eryG in Escherichia coli. J Bacteriol. May 1990;172(5):2541-6.

Reeves AR, Weber G, Cernota WH, Weber JM. Analysis of an 8.1-kb DNA fragment contiguous with the erythromycin gene cluster of Saccharopolyspora erythraea in the eryCl-flanking region. Antimicrob Agents Chemother. Dec. 2002;46(12):3892-9.

Rodicio MR, Chater KR. Small DNA-free liposomes stimulate transfection of streptomyces protoplasts. J Bacteriol. Sep. 1982:151(3):1078-85.

Roberts AN, Barnett L, Brenner S. Transformation of Arthrobacter and studies on the transcription of the Arthrobacter ermA gene in Streptomyces lividans and Escherichia coli. Biochem J. Apr 15, 1987;243(2):431-6.

Rodriguez L. Aguirrezabalaga 1. Allende N. Brana Af, Mendez C. Salas Ja. Engineering deoxysugar biosynthetic pathways from antibiotic-producing microorganisms. A tool to produce novel glycosylated bioactive compounds. Chem Biol. Jun. 2002;9(6):721-9.

Schwecke T, Aparicio JF, Molnar I, Konig A. Khaw LE, Haydock Sf, Oliynyk M, Caffrey P, Cortes J, Lester JB, et al. The biosynthetic gene cluster for the polyketide immunosuppressant rapamycin. Proc Natl Acad Sci USA. Aug. 15, 1995;92(17):7839-43.

Smith DB, Johnson KS. Single-step purification of polypeptides expressed in Escherichia coli as fusions with glutathione S-transferase. Gene. Jul. 15, 1988 ;67(1):31-40.

Tang L, Zhang YX, Hutchinson CR. Amino acid catabolism and antibiotic synthesis: valine is a source of precursors for macrolide biosynthesis in Streptomyces ambofaciens and Streptomyces fradiae.J Bacteriol. Oct. 1994;176(19):6107-19.

Vlasie MD, Banerjee R. Tyrosine 89 accelerates Co-carbon bond homolysis in methylmalonyl-CoA mutase. J Am Chem Soc. May 7, 2003;125(18):5431-5.

Ward JM, Janssen GR, Kieser T, Bibb MJ, Buttner, MJ, Bibb MJ. Construction and characterization of a series of multi-copy promoter-probe plasmid vectors for Streptomyces using the aminoglycoside phosphotransferase gene from Tn5 as indicator. Mol Gen Genet. Jun. 1986 ;203(3):468-78.

Weber JM, Wierman CK, Hutchinson CR. Genetic analysis of erythromycin production in Streptomyces erythreus. J Bacteriol. Oct. 1985;164(1):425-33.

Weber JM, Leung JO, Maine GT, Potenz RH, Paulus TJ, Dewitt JP. Organization of a cluster of erythromycin genes in Saccharopolyspora erythraea. J Bacteriol. May 1990; 172(5):2372-83.

Weber JM, Leung JO, Swanson SJ, Idler KB, Mcalpine JB. An erythromycin derivative produced by targeted gene disruption in Saccharopolyspora erythraea. Science. Apr. 5, 1991;252(5002):114-7.

Wu K, Chung L, Revill WP, Katz L, Reeves CD. The FK520 gene cluster of Streptomyces hygroscopicus var. ascomyceticus (ATCC 14891) contains genes for biosynthesis of unusual polyketide extender units. Gene. Jun. 13, 2000;251(1):81-90.

Xue Y. Wilson D, Sherman DH. Genetic architecture of the polyketide synthases for methymycin and pikromycin series macrolides. Gene. Mar 7, 2000;245(1):203-11.

Zhang W, Yang L, Jiang W, Zhao G, Yang Y, Chia J. Molecular analysis and heterologous expression of the gene encoding methylmalonyl coenzyme a mutase from rifamycin SV-producing strain Amycolatopsis mediterranei U32. Appl Biochem Biotechnol. Dec. 1999;82(3):209-25.

Weber, T.E., Schinckel, AP., Houseknecht, K.L., Richert, B.T. 2001. Evaluation of conjugated linoleic acid and dietary antibiotics as growth promotants in weanling pigs. J Anim Sci. 79:2542-2549. (Applicant IDS in 0006 file, signed by examiner Mar. 22, 2009).

Metzlaff. Biological Chemistry. "RNA-Mediated RNA Degradation in Transgene- and Virus-Induced Gene Silencing." Oct. 2002; 383(10): 1483-9. (USPTO ILL Document Delivery May 20, 2008).

Bruening. Proc. Natl. Acad. Sci. USA. "Plant gene silencing regularized," Nov. 1998;95: 13349-51. (USPTO ILL Document Delivery Sep. 23, 2005. ).

* cited by examiner

FIG. 2
(SEQ ID NO:1)

```
gcggtcgacg gcgccgagcc gtgggacgcc cccgagggca tcgcggtcaa gaacctctac      60
accgccgacg acctcgccga cgtcgacgcg ctcgacacct acccgggcct cgcgccgttc     120
ctgcgcggtc cctacccggc catgtacacg acccagccgt ggacgatccg ccagtacgcc     180
gggttctcga ccgccgagga gtcgaacgcg ttctaccgcc gcaacctcgc cgccggccaa     240
aagggcctct cggtcgcctt cgacctcgcg acgcaccgcg gctacgactc cgaccacccg     300
cgcgtgaagg gcgacgtcgg catggccggc gtcgcgatcg actcgatcta cgacgcccgc     360
cagctcttcg acggcatccc gctcgacgag atgagcgtct cgatgaccat gaacggcgcg     420
gtgctcccgg tgctcgcgct ctacatcgtg gcggccgagg agcaggggt gacgccggag     480
cagctctcgg ggaccatcca gaacgacatc ctcaaggagt tcatggtccg caacacctac     540
atctacccgc cggcgccgtc gatgcggatc atctccgaca tcttcgcgta cacggcggcg     600
aagatgccgc ggttcaactc catctccatc tccgggtacc acatccaaga ggccggggcg     660
acgaacgacc tcgagctcgc ctacacgctc gccgacggtg tggagtacat ccgcgccggg     720
ctcgacgtcg gcctcgacat cgacgcgttc gcgccgcggc tcagcttctt ctgggccatc     780
ggcatgaact tctacatgga gatcgcgaag atgcgcgccg cccgtgccct gwgggcccgg     840
ctcgtgcgcg acttcgaccc gaagaacccc aagagccTCa gcctgcgcac gcacagccag     900
acatcgggct ggagcctcac cgcgcaggac gtgttcaaca acgtccagcg cacctgcatc     960
gaggcgatgg ccgccacgca gggccacacc cagagcctgc acgaacgc gctcgacgag    1020
gcgatcgcgc tgccgacgga cttcagcgcg cggatcgccc gcaacacgca gctgctgctg    1080
cagcaggagt cgggcaccac cggcgtcatc gacccgtggg gcggctccta ctacgtcgag    1140
aagctgacgc acgacctcgc gaaccgcgcc tgggcgcaca tccaggaggt cgagaaggcc    1200
ggcggcatgg ccaaggccat cgaggcgggc atccccaaga tgcgcgtcga ggaggcggcc    1260
gcccgcacgc aggcacgcat cgactccggc cagcaggccg tcatcggcgt caacacctac    1320
cgcctcgccg acgaggaccc gctcgacgtg ctcaaggtcg acaacgcgtc ggtctacgcc    1380
cagcaggtgg cgaagctcga gcgactgcgc gccgagcgcg acccgcagga ggtcgagcgc    1440
gcgctcgacg ccctgacggc cagcgccgag cgtggcgcca gccgcgacgg ctcgctcgac    1500
ggcaacctgc tcgccctggc cgtcgacgcg gcccgcgcga aggcgacggt cggcgagatc    1560
tcctacgcgc tcgagaaggt ctacgggcgc caccaggccg tcatccgtac gatctccggt    1620
```

FIG. 2 cont'd

```
gtgtaccgga ccgaggcggg ccagggcggc aacgtccaga aggtcatcga cgccaccgag   1680
gcgttcgaga aggccgaggg tcgacgcccg cgcatcctcg tggccaagat gggccaggac   1740
ggccacgacc gcggccagaa ggtcatcgtc acggcgttcg ccgacatggg cttcgacgtc   1800
gacgtcggac cgctgttctc cacgcccgag gaggtcgcgc agcaggccgt ggacgccgac   1860
gtgcacatcg tcggcgtctc gagcctcgcg gcgggccacc tgacgctcct gccggagctg   1920
aagaaggcgt tggccgagct cggcggcgag gacgtcatgg tcgtcatggg tggcgtcatc   1980
ccgcccgacg acgtgccgac gctgaaggag atgggcgctg ccgaggtgtt cctgcccggc   2040
acggtcatcg ccgactccgc gctcagcctg ctcgagcggt ccgcgcgagc ctgcagcact   2100
agatggtcgg ttcgtccgag gtaa                                          2124
```

FIG. 3
(SEQ ID NO:2)

```
ctgtctctta tacacatctc aaccatcatc gatgaattcc accctgtgaa tgcgcaaacc     60
aaccettggc agaacatatc catcgcgtcc gccatctcca gcagccgcac gcggcgcatc    120
tcgggcagcg tgggtcctg gccacgggtg cgcatgatcg tgctcctgtc gttgaggacc    180
cggctaggct ggcggggttg ccttactggt tagcagaatg aatcaccgat acgcgagcga    240
acgtgaagcg actgctgctg caaaacgtct gcgacctgag caacaacatg aatggtcttc    300
ggtttccgtg tttcgtaaag tctggaaacg cggaagtcag cgccctgcac cattatgttc    360
cggatctatg tcgggtgcgg agaaagaggt aatgaaatgg cagatccctg gcttgttgtc    420
cacaaccgtt aaaccttaaa agctttaaaa gccttatata ttcttttttt tcttataaaa    480
cttaaaacct tagaggctat ttaagttgct gatttatatt aattttattg ttcaaacatg    540
agagcttagt acgtgaaaca tgagagctta gtacgttagc catgagagct tagtacgtta    600
gccatgaggg tttagttcgt taaacatgag agcttagtac gttaaacatg agagcttagt    660
acgtgaaaca tgagagctta gtacgtacta tcaacaggtt gaactgctga tcttcggatc    720
tatgtcgggt gcggagaaag aggtaatgaa atggcatccg gatctgcatc gcaggatgct    780
gctggctacc ctgtggaaca cctacatctg tattaacgaa gcaattcgaa ttcacagagg    840
cgcttatcgg tggccgcga gattcctgtc gatcctctcg tgcagcgcga ttccgaggga    900
aacggaaacg ttgagagact cggtctggct catcatgggg atggaaaccg aggcggaaga    960
cgcctcctcg aacaggtcgg aaggcccacc cttttcgctg ccgaacagca aggccagccg   1020
atccggattg tccccgagtt ccttcacgga aatgtcgcca tccgccttga gcgtcatcag   1080
ctgcataccg ctgtcccgaa tgaaggcgat ggcctcctcg cgaccggaga gaacgacggg   1140
aagggagaag acgtaacctc ggctggccct ttggagacgc cggtccgcga tgctggtgat   1200
gtcactgtcg accaggatga tccccgacgc tccgagcgcg agcgacgtgc gtactatcgc   1260
gccgatgttc ccgacgatct tcaccccgtc gagaacgacg acgtcccac gccggctcgc   1320
gatatcgccg aacctggccg ggcgagggac gcgggcgatg ccgaatgtct tggccttccg   1380
ctccccttg aacaactggt tgacgatcga ggagtcgatg aggcggaccg gtatgttctg   1440
ccgcccgcac agatccagca actcagatgg aaaaggactg ctgtcgctgc cgtagacctc   1500
gatgaactcc accccggccg cgatgctgtg catgagggc tcgacgtcct cgatcaacgt   1560
tgtctttatg ttggatcgcg acggcttggt gacatcgatg atccgctgca ccgcgggatc   1620
```

FIG. 3 cont'd

```
ggacggattc gcgatggtgt ccaactcagt catggtcgtc ctaccggctg ctgtgttcag    1680
tgacgcgatt cctggggtgt gacaccctac gcgacgatgg cggatggctg ccctgaccgg    1740
caatcaccaa cgcaaggggga agtcgtcgct ctctggcaaa gctccccgct cttccccgtc   1800
cgggacccgc gcggtcgatc cccgcatatg aagtattcgc cttgatcaga tcaggtaccc    1860
ggggatcatc ttattaatca gataaaatat ttctagattt cagtgcaatt tatctcttca    1920
aatgtagcac ctgaagtcag ccccatacga tataagttgt aattctcatg tttgacagct    1980
tatcatcgat aagctttaat gcggtagttt atcacagtta aattgctaac gcagtcaggc    2040
accgtgtatg aaatctaaca atgcgctcat cgtcatcctc ggcaccgtca ccctggatgc    2100
tgtaggcata ggcttggtta tgccggtact gccgggcctc ttgcgggata tcgtccattc    2160
cgacagcatc gccagtcact atggcgtgct gctagcgcta tatgcgttga tgcaatttct    2220
atgcgcaccc gttctcggag cactgtccga ccgctttggc cgccgcccag tcctgctcgc    2280
ttcgctactt ggagccacta tcgactacgc gatcatggcg accacacccg tcctgtggat    2340
cctctacgcc ggacgcatcg tggccggcat caccggcgcc acaggtgcgg ttgctggcgc    2400
ctatatcgcc gacatcaccg atggggaaga tcgggctcgc cacttcgggc tcatgagcgc    2460
ttgtttcggc gtgggtatgg tggcaggccc cgtggccggg ggactgttgg gcgccatctc    2520
cttgcatgca ccattccttg cggcggcggt gctcaacggc ctcaacctac tactgggctg    2580
cttcctaatg caggagtcgc ataagggaga gcgtcgaccg atgcccttga gagccttcaa    2640
cccagtcagc tccttccggt gggcgcgggg catgactatc gtcgccgcac ttatgactgt    2700
cttctttatc atgcaactcg taggacaggt gccggcagcg ctctgggtca ttttcggcga    2760
ggaccgcttt cgctggagcg cgacgatgat cggcctgtcg cttgcggtat tcggaatctt    2820
gcacgccctc gctcaagcct tcgtcactgg tcccgccacc aaacgtttcg gcgagaagca    2880
ggccattatc gccggcatgg cggccgacgc gctgggctac gtcttgctgg cgttcgcgac    2940
gcgaggctgg atggccttcc ccattatgat tcttctcgct tccggcggca tcgggatgcc    3000
cgcgttgcag gccatgctgt ccaggcaggt agatgacgac catcagggac agcttcaagg    3060
atcgctcgcg gctcttacca gcctaacttc gatcattgga ccgctgatcg tcacggcgat    3120
ttatgccgcc tcggcgagca catggaacgg gttggcatgg attgtaggcg ccgccctata    3180
ccttgtctgc ctccccgcgt tgcgtcgcgg tgcatggagc cgggccacct cgacctgaat    3240
```

FIG. 3 cont'd

```
ggaagccggc ggcacctcgc taacggattc accactccaa gaattggagc caatcaattc 3300
ttgcggagaa ctgtgaatgc gcaaaccaac ccttggcaga acatatccat cgcgtccgcc 3360
atctccagca gcgcacgcgg cgcatctcgg gcacgttggg tcctggaatt cgagctcggt 3420
accagcccga cccgagcacg cgccggcacg cctggtagat gtcggaccgg agttcgaggt 3480
acgcggcttg caggtccagg aaggggacgt ccatgcgagt gtccgttcga gtggcggctt 3540
gcgcccgatg ctagtcgccg ttgatcggcg atcgcaggtg cacgcggtcg atcttgacgg 3600
ctggcgagag gtgcgggagg atctgaccga cccggtccac acgtggcacc gcgatgctgt 3660
tgtgggctgg acaatcgtgc cggttggtag gatcctctag agtcgacgca tgcaagcttc 3720
tgcaggcatg caagcttcag ggttgagatg tgtataagag acag        3764
```

FIG. 4
(SEQ ID NO:3)

```
atgccccagg gccagccgct ggtcgtcccc gacgacggcc tcaccacccg ccagcgtcgc     60
aaccgtccgc tcgtcatggt ccacaccggg cccggcaagg ggaagtcgac cgccgcgttc    120
ggcctcgcca tgcgcgcctg gaaccagggc tggaaggtcg gcgtgttcca gttcgtgaag    180
tccgccaagt ggcgcgtcgg cgagcagagc gtgctcgagc acctgggccg cctgcacGAg    240
accgagggcc tcggcgggcc cgtcgagtgg cacaagatgg gctcgggctg gtcgtggtcg    300
cgcaagtcgg gcaccgacga cgaccacgcc gtcgccgccg ccgagggctg ggccgagatc    360
aagcgtcgcc tcgccaccga gacgcacgac ctctacgtgc tcgacgagtt cacctacccg    420
atgaagtggg gctgggtcga cgtcgacgac gtcgccgaca cgctcgcgtc gcgccccggc    480
cgccagcacg tggtgatcac cggccgcgac gccgcccccc ggctcctgga ggtcgccgac    540
ctcgtcaccg agatgacgaa ggtcaagcac cccatggacg tcggccagaa gggtcagcga    600
ggcatcgagt ggtga                                                    615
```

PROCESS OF INCREASING CELLULAR PRODUCTION OF BIOLOGICALLY ACTIVE COMPOUNDS

TECHNICAL FIELD OF THE INVENTION

The field of this invention is production of biologically active compounds by cells. More particularly, the present invention provides a process for increasing production of a biologically active compound derived from methylmalonyl-CoA. The process includes the step of inhibiting the activity of methylmalonyl-CoA mutase. The method is particularly useful for increasing the production of polyketide macrolide antibiotics in bacterial cells.

SEQUENCE LISTING

The nucleotide SEQUENCE LISTING recorded in computer readable form and provided concurrently herewith on CD-ROM is identical to the written SEQUENCE LISTING attached hereto and shown in FIGS. 2-4, and is incorporated herein by this reference.

SEQ ID NO 1, identical to that shown in FIG. 2, shows the nucleotide sequence of the wild-type gene for methylmalonyl-CoA mutase. The nucleotide sequence is shown in the 5' to 3' direction. As used herein, all of the letter designates for base pairs conforms to the standard set forth in 37 C.F.R. Section 1.822.

SEQ ID NO 2, identical to that shown in FIG. 3, shows the nucleotide sequence (also in the 5' to 3' direction) of the insertion transposon used to mutate the gene of SEQ ID NO 1 and the gene of SEQ ID NO 3.

SEQ ID NO 3, identical to that shown in FIG. 4, shows the nucleotide sequence (also in the 5' to 3' direction) of the wild-type gene for cobA.

BACKGROUND OF THE INVENTION

Despite the world's reliance on natural products from plants and microbes to treat and cure serious diseases, many fundamental questions remain to be answered as to how and why these medicines are produced in nature. Knowing more about the metabolism of these compounds will lead to simpler and more rational strategies for strain improvement. Strain improvement speeds up the drug development process and helps to reduce the cost of new drugs (Mateles, 2000).

An enormous array of medically important chemical structures are made in nature, particularly by plants and microbes. These structures fall into chemical classes based on shared routes of biosynthesis. One well-studied class of compounds is the polyketides, perhaps best characterized by the macrolide antibiotics, of which erythromycin is a primary example. Erythromycin and its derivatives, marketed under trade names such Biaxin®, Rulid®, and Zithromax®, are in wide use in the world today. Erythromycin's biosynthesis has been studied for over 50 years and so it is a widely used model system for secondary metabolite production.

Like many secondary metabolites, erythromycin is a tailored polymer. The building blocks are one molecule of propionic acid and 6 molecules of methylmalonic acid in their CoA forms (Omura, 1984). Tailoring steps include the addition of two sugars, the addition of a methyl group to one sugar, and the addition of two hydroxyl groups to the polyketide polymer backbone. Despite agreement on the identity of the chemical building blocks, scientists are still unsure of the source of the propionic acid and methylmalonic acid that are used to form the molecule. Knowing this key piece of information would help lead the way to development of genetic and process manipulations in order to boost production of the antibiotic.

Originally it was reported that succinyl-CoA is the major source of methylmalonyl-CoA via the enzyme methylmalonyl-CoA mutase (MCM) (Hunaiti and Kolattukudy, 1984). Propionyl-CoA was reported to come from decarboxylation of methylmalonyl-CoA (Hsieh and Kolattukudy, 1994). These early results implied that precursors for erythromycin biosynthesis are taken at the expense of central metabolism in a reverse-anaplerotic reaction. Consistent with these results, in a different macrolide producing host, when the mutAB genes, coding for MCM, were overexpressed, a macrolide antibiotic was overproduced (Zhang et al., 1999).

Amino acid catabolism has also been identified as an important source of precursors for macrolide biosynthesis (Omura et al., 1983, 1984; Dotzlaf et al., 1984). When branched chain amino acids such as valine, –isoleucine, leucine, or valine catabolites (propionate and isobutyrate) and threonine were added to the fermentation medium they boosted production of a macrolide antibiotic and its polyketide derived precursors (Omura et al., 1983, 1984, Tang et al., 1994). Conversely, when valine catabolism was blocked at the first step, (valine dehydrogenase, vdh), production of two different macrolide antibiotics went down 4-to-6-fold (Tang et al., 1994). These results pointed to amino acid catabolism, in particular branched-chain amino acid (BCAA) catabolism, as another vital source of macrolide antibiotic precursors in actinomycetes.

Surprisingly, when the branched-chain amino acid catabolic pathway was blocked at a later step in propionyl-CoA carboxylase, it did not lead to a reduction in macrolide production (Donadio et al, 1996). These results conflict with those of Dotzlaf et al, (1984), but they were obtained in a different macrolide-producing host and precursor feeding pathways have not yet been shown to operate universally in different hosts. Other workers also reported on this propionyl-CoA carboxylase reaction (Hunaiti and Kolatukuddy, 1982). Hsieh and Kolattukudy, 1994 cloned a gene that recent BLASTX analyses now shows could not code for a carboxylase, and may have been cloned by mistake.

Methylmalonyl-CoA mutase, coded for by the mutAB gene pair, was originally cited by Hunaiti and Kolattukudy (1984) to be the key enzyme to provide methylmalonyl-CoA for erythromycin biosynthesis.

According to the conclusions of Hunaiti and Kolattukudy (1984) and Zhang et al., (1999) whose results indicated the source of methylmalonyl-CoA to be from succinyl-CoA, one would predict that a block in mutB should reduce or block production of the erythromycin. This direction for methylmalonyl-CoA mutase, though, is often referred to as the "reverse" direction, because the forward—or anaplerotic—direction towards succinyl-CoA is favored enzymatically by a factor of twenty to one (Kellermeyer, et al., 1964; Vlasie and Banerjee, 2003).

BRIEF SUMMARY OF THE INVENTION

In one aspect, the present invention provides a method of increasing the production of a biologically active compound in a cell. The biologically active compound is derived at least in part from methylmalonyl-CoA. The method includes the step of inhibiting the activity of methylmalonyl-CoA mutase in the cell.

The biologically active compound can be an immunosuppressant such as rapamycin, FK506, FK520, or ascomycin.

The biologically active compound can be an antifungal agent such as rapamycin, candicidin or soraphen.

The biologically active compound can be an antiparasitic agent such as avermectin.

The biologically active compound can be an antibiotic such as a polyketide antibiotic. A preferred polyketide antibiotic is a macrolide polyketide antibiotic such as erythromycin, tylosin, niddamycin, spiramycin, oleandomycin, methymycin, neomethymycin, narbomycin, pikromycin, or lankamycin.

The biologically active compound can be an animal feed promotant such as a monensin as exemplified by monensin A or monensin B.

A cell can be a prokaryotic or eukaryotic cell. A preferred prokaryotic cell is a bacterial cell. Preferred and exemplary bacterial cells are *Saccharopolyspora*, *Aeromicrobium* and *Streptomyces*. Particularly preferred bacterial cells are *Saccharopolyspora erytlrea*, *Aeromicrobium erythreum*, *Streptomyces fradiae*, *Streptomyces avernitilis*, *Streptomyces cinnanionensis*, *Streptomyces antibioticus*, *Streptomyces venezuelae*, *Streptomyces violaceoniger*, *Streptomyces hygroscopicus*, *Streptomyces* spp. FR-008, and *Streptomyces griseus*.

The cell can also be a eukaryotic cell such as a plant cell or an animal cell. A preferred animal cell is a mammalian cell.

Any means of inhibiting the activity of methylmalonyl-CoA mutase can be used in a present method. In one embodiment, methylmalonyl-CoA mutase activity is inhibited by decreasing or reducing the level of a co-factor necessary for methylmalonyl-CoA mutase activity. One such necessary co-factor is co-enzyme B12. The level of co-enzyme B12 can be reduced by inhibiting transcription of a gene that encodes an enzyme used in the biosynthesis of that co-factor. Examples of such genes are the cob genes, of which the cobA gene is described below.

Another means of inhibiting the activity of methylmalonyl-CoA mutase is to inhibit the transcription of the gene for methylmalonyl-CoA mutase. An exemplary means for inhibiting transcription is through the use of DNA binding proteins such as zinc fingers.

Yet another means for inhibiting the activity of methylmalonyl-CoA mutase is through mutation of the gene for methylmalonyl-CoA mutase. Mutating the gene methylmalonyl-CoA mutase can result in expression of a gene product that encodes an inactive form of the the enzyme. Means for mutating genes are well known in the art. One such means for mutating methylmalonyl-CoA mutase and inhibiting the activity of methylmalonyl-CoA mutase is set forth hereinafter in the Examples. Mutating can be accomplished in vitro using means well known in the art.

In a preferred embodiment, the present invention provides a process for increasing the production of an antibiotic in a bacterial cell. The antibiotic is preferably a polyketide macrolide antibiotic and, even more preferably erythromycin. The bacterial cell is preferably a *Saccharapolyspora* or *Aeromicrobium*, and, more preferably *Saccharapolyspora erythraea* or *Aeromicrobium erythreum*.

In another aspect, the present invention provides a mutated methylmalonyl-CoA mutase gene. Preferably, that mutated gene has the nucleotide sequence shown in SEQ ID NO:1. Also provided are expression vectors containing that nucleotide sequence and cells containing the expression vector or nucleotide sequence. A preferred such cell is a bacterial cell.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings that form a portion of the specification, in which:

FIG. 2 (also referred to as FIG. 2 or FIG. 2) shows the nucleotide sequence of the wild-type gene for methylmalonyl-CoA mutase. The nucleotide sequence is shown in the 5' to 3' direction. As used herein, all of the letter designates for base pairs conforms to the standard set forth in 37 C.F.R. Section 1.822. The base pairs illustrated in bold-face type (bolded) indicate the point of insertion for the transposon of FIG. 3.

FIG. 3 (also referred to as FIG. 3 or FIG. 3) shows the nucleotide sequence (also in the 5' to 3' direction) of the insertion transposon used to mutate the gene of FIG. 2 and the gene of FIG. 4.

FIG. 4 (also referred to as FIG. 4 or FIG. 4) shows the nucleotide sequence (also in the 5' to 3' direction) of the wild-type gene for cobA. The base pairs illustrated in bold-face type (bolded) indicate the point of insertion for the transposon of FIG. 3.

DETAILED DESCRIPTION OF THE INVENTION

Figure 1:
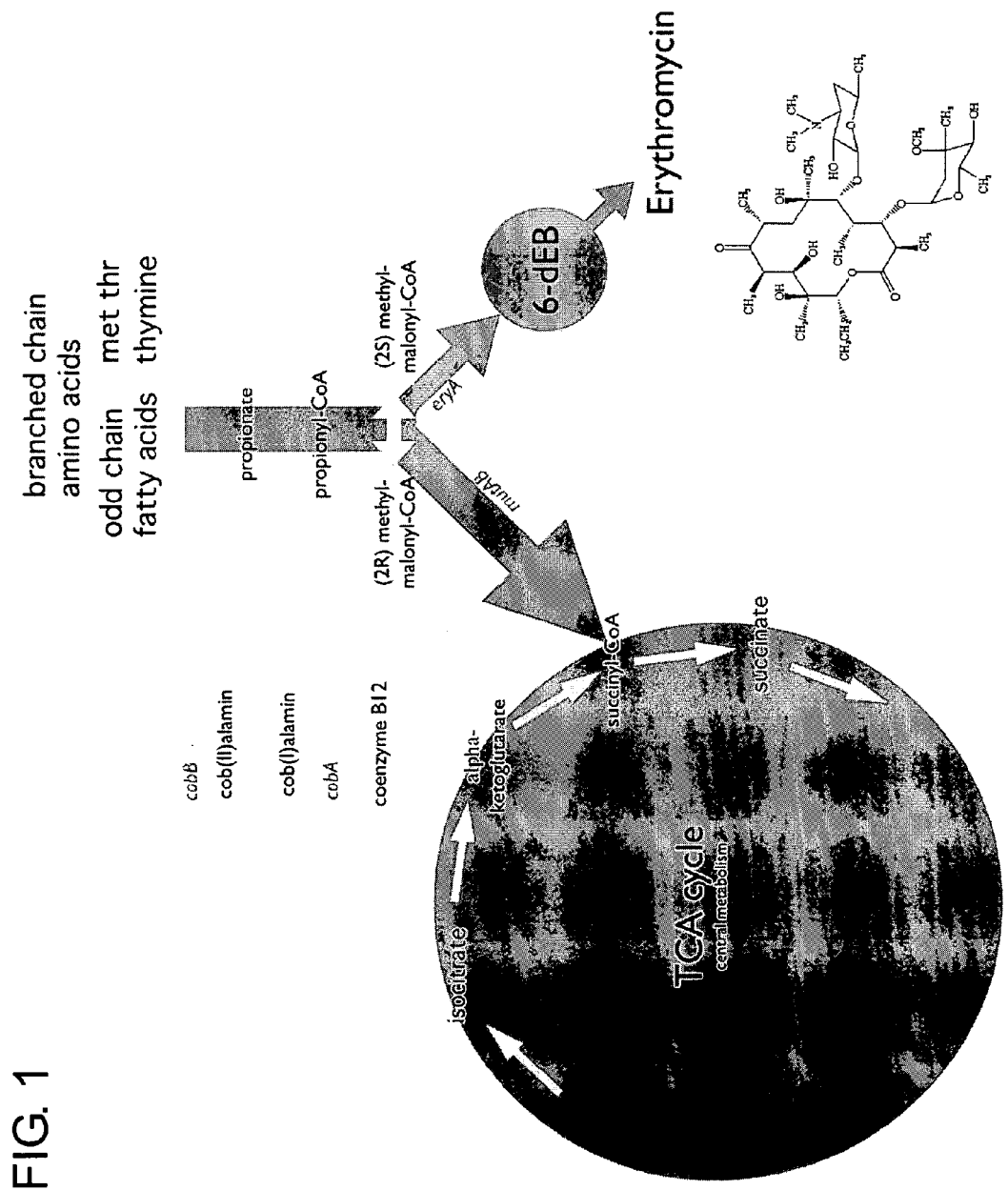
FIG. 1 (also referred to as FIG. 1 or FIG. 1) shows a schematic diagram of methylmalonyl-CoA metabolism.

While the present invention is susceptible of embodiment in many different forms, there are shown in the drawings and will be described herein in detail specific examples and embodiments thereof, with the understanding that the present disclosure is to be considered as an exemplification of the principles of the invention and is not intended to limit the invention to the specific examples and embodiments illustrated.

The Detailed Description portion of this disclosure will conclude with a References Section for the citations to the indicated references of the disclosure, followed by the claims.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, eg., Watson et al. *Molecular Biology of the Gene*, 4th Edition, 1987, The Bejacmin/Cummings Pub. co., p. 224).

As used herein, "expression vector" refers to a plasmid, virus or other vehicle known in the art that has been manipulated by insertion or incorporation of heterologous DNA, such as nucleic acid encoding the fusion proteins herein or expression cassettes provided herein. Such expression vectors contain a promotor sequence for efficient transcription of the inserted nucleic acid in a cell. The expression vector typically contains an origin of replication, a promoter, as well as specific genes that permit phenotypic selection of transformed cells. As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors". Also included are vectors that allow cloning of cDNA (complementary DNA) from mRNAs produced using reverse transcriptase.

As used herein, "host cells" are cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, isolated with reference to a nucleic acid molecule or polypeptide or other biomolecule means that the nucleic acid or polypeptide has separated from the genetic environment from which the polypeptide or nucleic acid were obtained. It may also mean altered from the natural state. For example, a polynucleotide or a polypeptide naturally present in a living animal is not "isolated", but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:31-40. The terms isolated and purified are sometimes used interchangeably.

Thus, by "isolated" the nucleic acid is free of the coding sequences of those genes that, in a naturally_occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Isolated or purified as it refers to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange chromatography, affinity chromatography, density gradient centrifugation and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

The Invention

The present invention provides a method of increasing the production of a biologically active compound in a cell. The biologically active compound is derived at least in part from methylmalonyl-CoA. The method includes the step of inhibiting the activity of methylmalonyl-CoA mutase in the cell.

Biologically Active Compound

As used herein, the phrase "biologically active compound" means any compound having an effect on a living organism. The biologically active compound is derived, at least in part, from methylmalonyl-CoA. As is well known in the art, biologically active compounds that are derived from methylmalonyl-CoA have methylmalonic acid incorporated into the compound structure.

Biologically active compounds derived, at least in part, from methylmalonyl-CoA are well known in the art. Such compounds include antiparasitics, antifungals, immunosuppressants, feed growth promotants and antibiotics. Table 1, below, summarizes exemplary such compounds.

TABLE 1

| | | | |
|---|---|---|---|
| Erythromycin | *Saccharopolyspora erythraea*, *Aeromicrobium erythreum* | 14-member macrolide antibiotic | Weber et al., 1991 |
| Tylosin-Niddamycin-Spiramycin | *Streptomyces fradiae* | 16-member macrolide antibiotic | Omura et al., 1977 |
| Avermectin | *Streptomyces avermitilis* | Antiparasitic | Ikeda et al., 1999 |
| Monensin | *Streptomyces cinnamonensis* | Animal feed growth promotant | Liu et al., 1999 |
| Oleandomycin | *Streptomyces antibioticus* | 14-member macrolide antibiotic | Rodriguez et al., 2002 |
| methymycin, neomethymycin, | *Streptomyces venezuelae* | 12-member macrolide antibiotic | Xue et al., 2000 |
| narbomycin and pikromycin | *Streptomyces venezuelae* | 14-member macrolide antibiotic | Xue et al., 2000 |
| Lankamycin | *Streptomyces violaceoniger* and *Streptomyces rochei* | 14-member macrolide antibiotic | Mochizuki et al., 2003 |
| Rapamycin | *Streptomyces hygroscopicus* | Immuno-suppressant and antifungal agent | Schwecke et al., 1995; Aparicio, et al., 1996; Molnar et al., 1996; Haydock et al., 1995. |
| FK520, ascomycin | *S. hygroscopicus* | Immuno-suppressant | Wu et al., 2000 |
| Candicidin | *Streptomyces* spp. FR-008; *Streptomyces griseus* | Antifungal | Hu et al., mol microbial, 1994; Aparicio et al, 2003; Gil J A, Campelo-Diez A B, 2003 |
| Soraphen | *Sorangium cellulosum* | Antifungal | Gerth K J. Antibiotics 47: 23 (1994) |

A particularly preferred biologically active compound whose production can be increased by a present process is an antibiotic. Exemplary antibiotics are polyketide antibiotics. More preferably, antibiotics are polyketide, macrolide antibiotics. Polyketide macrolide antibiotics are well known in the art. Exemplary and preferred such antibiotics are erythromycin, tylosin, niddamycin, spiramycin, oleandomycin, methymycin, neomethymycin, narbomycin, pikromycin, and lankamycin.

Cells

The production of a biologically active compound can be increased in any cell that contains anabolic and catabolic pathways involving methylmalonyl-CoA. A schematic diagram showing such metabolic pathways is shown in FIG. 1. Numerous such cells are well known in the art. The cell can be a prokaryotic or a eukaryotic cell. Exemplary prokaryotic cells are #1 Domain Archaea (halophiles, methanogens, thermophiles) and #2 Domain Bacteria (cocci, bacilli, spirochetes). Bacterial cells are particularly preferred. Exemplary bacterial cells are *Saccharopolyspora*, *Aeromicrobium* and *Streptomyces*. Particularly preferred bacterial cells are *Saccharopolyspora erytilraea*, *Aeromicrobium erythreum*, *Streptomyces fradiae*, *Streptomyces avermitilis*, *Streptomyces cinnamonensis*, *Streptomyces antibioticus*, *Streptomyces venezuelae*, *Streptomyces violaceoniger*, *Streptomyces hygroscopicus*, *Streptomyces* spp. FR-008, and *Streptomyces griseus*.

Exemplary eukaryotic cells are listed below.

3 Green Algae (Chlorobionts)—Domain Eukarya:Kingdom Protista:Division Chlorobionts #4 Amoeba (a Protozoan)—Domain Eukarya:Kingdom Protista:Rhizopod Sarcodines #5 Dictyostelium (Cellular Slime Mold)—Domain Eukarya:Kingdom Protista:Division Arasiomycota #6 Lichen—Domain Eukarya:Kingdom Fungi:Division Mycomycota #7 Zygomycota—Domain Eukarya:Kingdom Fungi: Division Zygomycota #8 Ascomycota—Domain Eukarya: Kingdom Fungi:Division Ascomycota #9 Bryophytes— Domain Eukarya:Kingdom Plantae:Division Bryophyta #10 Horsetail Fern (A Seedless Vascular Plant)—Domain Eukarya:Kingdom Plantae:Division Sphenophyta #11 Ginkgo—Domain Eukarya:Kingdom Plantae:Division Ginkgophyta #12 Conifers (Gymnosperms)—Domain Eukarya:Kingdom Plantae:Division Coniferophyta #13 Angiosperms (Flowering Plants)—Domain Eukarya:Kingdom Plantae:Division Anthophyta #14 Porifera (Sponges)— Domain Eukarya:Kingdom Animalia:Phylum Porifera #15 Corals (Cnidarian Polyps)—Domain Eukarya:Kingdom Animalia:Phylum Cnidaria:Class Anthozoa #16 Jellyfish (Cnidarian Medusas)—Domain Eukarya:Kingdom Animalia: Phylum Cnidaria:Class Schphozoa #17 Platyhelminthes (Flatworms)—Domain Eukarya:Kingdom Animalia:Phylum Platyhelminthes #18 Mollusca—Domain Eukarya:Kingdom Animalia:Phylum Mollusca #19 Chiton—Domain Eukarya: Kingdom Animalia:Phylum Mollusca:Class Polyplacophora #20 Annelida (Segmented Worms)—Domain Eukarya:Kingdom Animalia:Phylum Annelida #21 Arthropoda—Domain Eukarya:Kingdom Animalia:Phylum Arthropoda #22 Horseshoe Crab (An Arthropod)—Domain Eukarya:Kingdom Animalia:Phylum Arthropoda:Class Cheliceramorpha #23 Echinodermata—Domain Eukarya:Kingdom Animalia:Phylum Echinodermata #24 Holithuriudea—Domain Eukarya:Kingdom Animalia:Phylum Echinodermata:Class Holithuriudea #25 Sea Urchin (An Echinoderm)—Domain Eukarya:Kingdom Animalia:Phylum Echinodermata:Class Echinoidea #26 Chordata—Domain Eukarya:Kingdom Animalia :Phylum Chordata #27 Amphioxus (Lancelet)—Domain Eukarya:Kingdom Animalia :Phylum Chordata:Subphylum Cephalachordata #28 Agnatha (A Jawless Vertebrate)—Domain Eukarya:Kingdom Animalia:Phylum Chordata:Subphylum Vertebrata:Class Agnatha #29 Chondrichthyes (Cartilaginous Fishes)—Domain Eukarya:Kingdom Animalia:Phylum Chordata:Subphylum Vertebrata:Class Chondrichthyes #30 Osteichthyes (Bony Fishes)—Domain Eukarya:Kingdom Animalia:Phylum Chordata:Subphylum Vertebrata:Class Osteichthyes #31 Amphibia—Domain Eukarya:Kingdom Animalia:Phylum Chordata:Subphylum Vertebrata:Class Amphibia #32 Reptilia—Domain Eukarya:Kingdom Animalia:Phylum Chordata:Subphylum Vertebrata:Class Reptilia #33 Aves (Birds)—Domain Eukarya:Kingdom Animalia: Phylum Chordata:Subphylum Vertebrata:Class Aves #34 Mammalia—Domain Eukarya:Kingdom Animalia:Phylum Chordata:Subphylum Vertebrata:Class Mammalia.

Inhibiting Methylmalonyl-CoA Mutase

A process of the present invention includes the step of inhibiting the activity of methylmalonyl-CoA mutase, the enzyme that catalyzes the interconversion of methylmalonyl-CoA and succinyl-CoA (See FIG. 1).

The activity of methylmalonyl-CoA mutase can be inhibited in a number of ways. Any means of inhibiting that result in a decreased catalytic capacity of the enzyme can be used in the subject invention. By way of example, the enzyme can be contacted with an enzyme inhibitor, a substance that binds to the enzyme and interferes with its ability to interact with substrate conversion. By way of further example, enzyme activity can be inhibited by decreasing the availability of any co-factor necessary for such activity.

It is well known in the art that co-enzyme B12 is a co-factor for methylmalonyl-CoA mutase activity. Thus, means for decreasing the availability of co-enzyme B12 can be used to inhibit the mutase activity. As is well known in the art, the genes responsible for coenzyme B12 biosynthesis are the cob genes. Levels of coenzyme B12 can be reduced by inhibiting the transcription of the cob genes. Means for inhibiting gene transcription are well known in the art.

The activity of methylmalonyl-CoA mutase (MCM) can be inhibited by decreasing or inhibiting the transcription of a gene that encodes the enzyme. Such genes are well known in the art. In most bacteria, with *E. coli* being a notable exception (Dayem et al., 2002), MCM is a heterodimer coded for by the mutAB gene pair (Marsh et al., 1989, Birch et al., 1993). A similarity between human and bacterial metabolism is in keeping with a theme further evidenced by the conservation of amino acid sequence in methylmalonyl-CoA mutases across the biological spectrum. BLAST analysis revealed 64% identity in amino acid sequence between the mutB gene of *A. erythreum* and the equivalent human amino acid sequence. A high degree of identity exists to all other mutB genes in the database.

The transcription of MCM can be inhibited using means well known in the art. By way of example, DNA binding proteins such as zinc fingers are known to bind to and inhibit transcription of genes (See, e.g., U.S. Pat. No. 6,140,466). A preferred means for inhibiting MCM activity is to mutate the gene for wild-type MCM such that the expressed gene product of the mutated gene is an inactive form of the enzyme. Means for mutating genes are well known in the art.

As described in detail hereinbelow in the Examples, mutation of a gene for wild-type MCM resulted in inhibition of MCM activity and an increased production of erythromycin. Using tagged mutagenesis, microfermentation screening, and a simple agar plate bioassay method to measure the production of antibiotic in the growth medium, mutants were found that made 50-100% more erythromycin than the parent strain. Of the seven highest producing mutants, three were determined to carry transposon insertions in mutB, a gene coding for the alpha subunit of methylmalonyl-CoA mutase. Four other mutants carried transposon insertions in both orientations in cobA, an adenosyl transferase involved in vitamin $B_{12}$ biosynthesis.

The mutB strains all carried transposon insertions in the same orientation and exact same site of the mutB gene, indicating that the gene carries a hot spot for insertion of Tn5. This was also the case for cobA insertions, except that for in cobA we found both orientations of the transposon in the same site. Both mut and cob mutations appeared in the library at frequencies that were more than three times greater than would be expected by chance from the total of 3,049 mutants that were screened.

Insertional inactivation of *A. erythreum* genes was performed using a derivative of the transposon Tn5 (Goryshin and Reznikofff, 1998). The plasmid was designed to function in both *E. coli* and *A. erythreum* with suitable drug resistance markers, origins of replication, and a promoter known to cause increased expression in other high G+C Actinomycetes. The functional portions of the plasmid in *A. erythreum* are the tsr gene, conferring thiostrepton resistance and ermE* promoter. Previous studies on *A. erythreum* have shown that the ColE1 origin does not function in *A. erythreum* and therefore plasmids based on this origin of replication can be used as integration vectors. It is not known whether the R6Kγ ori is functional in this host. The strategy was to generate both knockout mutants by gene replacement of the Tn cassette as well as potential hyperexpression mutants which would overexpress downstream genes from the inserted ermE* promoter located at one end of the transposon.

For transposon plasmid construction, pUC19 was digested with PvuII and the larger (2.3 kb) fragment was ligated to EZ::TN™<TET-1> to generate pFL3010. This plasmid contained the 19 bp mosaic ends recognized by the Tn5 transposase and the $Tet^r$ gene for selection in *E. coli*. To select for *A. erythreum* transformants the tsr gene from pFL8 (Reeves et al., 2002) was cloned into the EcoRI and KpnI sites of pFL3010, generating pFL3012. To generate mutant strains which overexpress genes located downstream of the Tn insertion site the ermE* promoter (Bibb et al. 1994) was ligated to MscI and PstI-digested pFL3012. The ermE* promoter was obtained by digesting pIJ4070 (Bibb et al. 1994) with MscI and PstI. This construct was designated pFL2083. Finally, to retrieve plasmids from the *A. erythreum* chromosome for sequence analysis of the Tn insertion site and the adjacent genomic DNA the conditional origin of replication R6Kγ was ligated into the EcoRI site of pFL2083. The R6Kγ origin was obtained by amplification of an 800 bp fragment from EZ::TN™<R6Kγori/Kan-2> with engineered EcoRI sites at the 5' ends. This construct was designated pFL2087 and was used in all in vitro Tn mutagenesis reactions.

*E. coli* library of *A. erythreum* genomic DNA. The plasmid library was constructed in the *A. erythreum* integration vector pFL2082, a pUC19-derived vector containing the aphI gene from Tn903. The aphI gene is expressed at low level in *A. erythreum* and confers kanamycin resistance up to about 10-15 μg/ml with good growth. *A. erythreum* is normally sensitive to kanamycin at levels as low as 2 μg/ml. pFL2082 contains a unique BamHI site that was used to ligate *A. erythreum* Sau3A1 chromosomal fragments in the 8-20 kb range. Several different vector preparations were dephosphorylated with different concentrations of CIAP or SAP in order to obtain the highest ratio of white to blue colonies after ligation. Only those ligations that resulted in a white to blue colony ratio of approximately 10 were used in later experiments. To generate a library that represented in excess of 5-fold coverage of the chromosome (estimated *A. erythreum* genome size somewhere between 4-8 Mb, representing about 4,000-8,000 coding sequences), 100,000 white colonies were harvested into 25 pools. This large number of colonies was chosen based on the assumption that some genes will be disproportionately represented over others after selection in *E. coli*. The colonies were split among 25 pools (ca. 4,000 colonies/pool) to increase randomness. To determine the insert size of random plasmid isolates a total of 65 white colonies were analyzed by restriction analysis of their plasmid DNA. EcoRI and HindIII double digestions showed that in all but four cases the average insert size was 14.0 kb. This library was designated *A. erythreum* genomic library or library 1.

In vitro transposon mutagenesis was performed separately with 5 μg of total DNA from each of the 25 genomic library pools. After mutagenesis and transformation, the *E. coli* cells were plated on agar containing tetracycline (Tet), ampicillin (Ap), and kanamycin (Kn). The three antibiotics were used together to select for the transposon insertion (Tet marker) and to enrich for plasmids that contain insertions in the *A. erythreum* DNA by eliminating $Ap^S$ or $Kn^S$ strains. The ratio of white to blue colonies increased dramatically after transposon mutagenesis from about 10 to greater than 25. Blue colonies from the genomic DNA library contained plasmids that were religated pFL2082. The increase in the ratio of white to blue colonies on Tet, Ap, Kn plates was due to the increased probability of the transposon inserting into a larger plasmid without affecting Ap or Kn resistance. Blue colonies that were $Tet^r$ $Ap^r$ $Kn^r$ represented plasmids containing the transposon in a neutral site in pFL2082. A total of 50,000 $Tet^r$ $Ap^r$ $Kn^r$ white colonies were harvested into pools containing about 2,000 colonies/pool corresponding to the previously generated 25 genomic library pools. This library was designated *A. erythreum* Tn mutagenesis library or library 2. To confirm that the transposon had inserted into the genomic library DNA, 25 random $Tet^r$ $Ap^r$ $Kn^r$ plasmids from white colonies were analyzed by restriction analysis using EcoRI and HindIII in double digestions and HindIII in single digestions. All 25 plasmids contained transposon DNA along with an average of 15 kb of *A. erythreum* genomic DNA. The control plasmids, pFL2082 only (2 HindIII sites) and plasmids from blue $Tet^r$ $Ap^r$ $Kn^r$ colonies (2 HindIII sites), gave the expected restriction patterns (data not shown). In all but one case, a single transposon insertion occurred.

Initial transformation experiments using Tn mutagenesis library DNA and *A. erythreum* B-3381 protoplasts were performed using a modified procedure originally described by Roberts et al. (1987) The most important modification to the procedure was in the handling of the DNA before transformation. Previous studies by Miller et al. (1991) showed that integrative transformation based on homologous recombination was a rare event in *A. erythreum*. In that study, undenatured plasmid DNA was used. The subsequent recombination frequency observed was very low (3 $Kn^r$ colonies were obtained per 2 μg of DNA). This recombination frequency would not be suitable for generating a random knockout library. Oh and Chater (1997) demonstrated that denaturing DNA with NaOH before protoplast transformation led to a significant increase in the number of *S. coelicolor* $A(3)_2$ transformants and proposed that this may also hold true for other organisms. To test if this would be the case with *A. erythreum*, 9 pools of alkaline denatured library DNA were transformed separately with selection for $Thio^r$ colonies. The results showed that the number of $Thio^r$ transformants observed when protoplasts were transformed with denatured DNA increased 2-3 orders of magnitude per μg of DNA when compared to undenatured DNA controls. Approximately 100-500 $Thio^r$ transformants were obtained per regeneration plate per 4 μg of denatured DNA. A total of 828 Thio$^r$ transformants were isolated per pool and stored as glycerol stocks in microtiter dishes at −80° C., along with parent controls. To determine the frequency of mutants derived by single crossover insertion and gene (marker) replacement a total of 4,912 Thio$^r$ mutants from all 9 pools were screened for kanamycin resistance. The results showed that a significant majority (88.2%) of the mutants were derived by single crossover insertion (Thio$^r$Kn$^r$). Why the frequency of gene replacement (11.8%, Thio$^r$ Kn$^s$) was so low is not known. Most single crossover mutants would not generally exhibit a knockout phenotype, except in cases of polarity due to the insertion. This library was still useful because of the presence of the ermE* promoter at the end of the transposon and was subsequently screened for mutants exhibiting an altered erythromycin production level. In this study, we were mainly interested in analyzing recombinants derived by gene replacement and therefore we needed to develop a simple visual screen to directly distinguish between these two classes of mutants on the regeneration plate.

To generate a gene replacement library we developed a rapid, simple visual screen that took advantage of the Kn$^r$ phenotype of single crossover mutants and the Kn$^s$ phenotype of gene replacement mutants. Kanamycin sulfate normally inhibits the growth of wild type A. erythreum when cells are exposed to concentrations of the antibiotic at 5 μg/ml or above. Mutants containing the aph1 gene are resistant to kanamycin up to a concentration of about 10-15 μg/ml while maintaining good growth. Tetrazolium chloride (tetra red) diffuses into A. erythreum cells after exposure to an agar underlay containing the dye after about 2-3 hours and eventually (between 24-48 hr) turns colonies orange to dark red. To test whether we could observe a difference between single crossover and gene replacement mutants on the basis of colony size, colony color or both after exposure to kanamycin and tetra red supplemented agar we transferred layers from 2-day post underlay plates to fresh 2×YTG plates containing kanamycin at 20 μg/ml and tetra red. Mutants that have undergone gene replacement would be Kn$^s$ and stop growing whereas single crossover mutants would be Kn$^r$ and continue to grow. At the time of underlay with the Kn/tetra red agar all the transformants are uniformly yellow. Twenty-four hr post underlay all colonies have incorporated the tetra red and are uniformly orange-red. Approximately 40-44 hours post underlay certain colonies have stopped growing and become dark red whereas the majority of colonies have become larger and have diluted the dye to a light orange. To measure colony sizes before and after the underlay, plates were digitally photographed at one day intervals beginning at time zero (equal to the time of underlay) for 7 days. Colonies that turned orange continued to grow throughout the 7-day period and colonies that were dark red at 24-48 hr post underlay remained so. These results suggested that the dark red colonies were Kn$_s$ and possibly mutants derived by gene replacement. To test the antibiotic resistance phenotype of individual colonies, 50 dark red and 50 orange colonies were replica patched onto 2×YTG plates supplemented with Thio and Kn or no antibiotic. The results showed that 92% of the dark red colonies were Thio$^r$ Kn$^s$ and 100% of the orange colonies were Thio$^r$ Kn$^r$. PCR was used to confirm the presence of the tsr gene in 20 of the Thio$^r$ Kn$^s$ strains. All but one of the strains contained the tsr gene. Based on these results we generated a library of mutants using the colorimetric plate assay to select for gene replacement mutants using Tn mutagenesis DNA from pools 8-12. A total of 782 dark red colonies were identified (representing about 10% of the total scored) and patched onto antibiotic selection plates for testing drug resistance. Analysis of the patch plates showed that 82.1% of the colonies consisted of Kn$^s$ Thio$^r$ isolates and 17.9% consisted of Kn$^r$ Thio$^r$ isolates. Some of the 17.9% of Thio$^r$ Kn$^r$ "red" colonies are actually mixtures of single crossover and gene replacement mutants, since Kn$^r$ strains can grow into the Kn$^s$ strains and therefore make isolation difficult. PCR of 20 random plasmids derived from Kn$^s$ Thio$^r$ isolates showed that all contained the tsr gene, indicating that the colorimetric assay is efficient at identifying on the regeneration plate A. erythreum mutants derived by gene replacement.

To determine if the Tn mutagenized library inserted randomly into the A. erythreum chromosome we characterized it according to three criteria: i) Southern blotting of insertion mutants; ii) sequence analysis of DNA adjacent to the Tn insertion site; and iii) the frequency and location of low erythromycin producers (Ery down) and erythromycin non-producing mutants. Southern blot analysis was performed on 15 mutants digested with XhoI and BamHI using a Thio$^r$ Tet$^r$ gene probe obtained from SphI/EcoRI digestion of pFL2083. DNA from two different sets of mutants were used, neighboring isolates from the same glycerol stock plate in the same row and random strains exhibiting an altered erythromycin yield. XhoI was selected since it does not cut within the transposon and yields a single hybridizing band. The first set contained nine consecutive mutants derived from pool 4, plate 2, row B, well positions 1-9, whereas the second set contained six mutants that exhibited either an increase, decrease or non-producing erythromycin phenotype from 6 different plates. The results showed that most, if not all, of the 9 mutants obtained from the same plate contained insertions at different chromosomal locations. It is possible that the DNA from the mutants contain the same insert, but without further analysis the precise location of the insertions remains unknown. These results show that there is not a strong bias ("hotspots") for Tn5 insertion sites when exposed to A. erythreum DNA. Of the six mutants with an altered erythromycin yield five of the six inserted at different locations in the chromosome and two appeared that they might be similar. Later, sequence analysis revealed that the transposon had inserted into the same site in these two mutants but in the opposite orientation.

Analysis of DNA sequences adjacent to the insertion site in 20 mutants revealed that the transposon had integrated randomly in the A. erythreum chromosome, except in seven high erythromycin-producing (Ery up) strains. In four of these mutants the insertion had occurred in the same site but in opposite orientations. In the other three mutants the insertion occurred in the site an in the same orientation. As expected, all sequences immediately flanking the insertion site contained the 9-bp duplication characteristic of Tn5 transposition. Analysis of 10 different 9-bp target sequences revealed a general similarity to the consensus sequence proposed by Goryshin et al., 1998, but no exact matches were found. However, the fact that we isolated the same insertion mutant from independent pools in all seven mutants suggests that there was a base preference occurring at certain positions during the in vitro transposition reaction.

A total of 14 non-producing mutants and 15 very low (<40 μg/ml) erythromycin producing strains were generated in this study. Null mutants would arise if the insertion occurred in the eroA cluster, which encodes the polyketide backbone or in genes involved in regulating the expression of the eroA genes or secondary metabolism. Mutants producing low levels of bioactivity would arise from insertions in the erythromycin tailoring enzymes or mutations that affect the general physiology of the cell. The ero biosynthetic gene cluster has been sequenced and has been determined to be approximately 60 kb. Assuming that the *A. erythreum* chromosome is somewhere between 4-8 Mb, then the cluster would comprise between 0.75%-1.5% of the total chromosome. In this study, we screened 3,049 mutants for erythromycin production. If the library were completely random, we would expect somewhere between 23-46 null or low producing mutants. We obtained 29 such mutants, which represented 0.95% of the total isolates screened. We conclude from the results of these 3 analyses that the *A. erythreum* Tn mutagenized library is random.

Approximately 54% (3,049/5,694) of the mutants from the 2 libraries, 2,267 from pools 1-5 of the initial library and all 782 mutants from the gene replacement library were screened in duplicate microfermentations for their erythromycin production. A total of 26 mutants were analyzed by BLASTX analysis of the retrieved gene or plasmid sequences disrupted by the insertion from strains exhibiting an altered erythromycin yield. Of the 3,049 mutants tested, 28 mutants (~1%) produced greater than 50% above the parent control strain and were analyzed further. These 28 mutants were grouped into single crossover mutants (3) and gene replacement mutants (25), hereafter designated Ery-up mutants. All the Ery-up mutants were subjected to microfermentations where the number of replicates ranged from N=24 to N=96. Strains that maintained a 50% increase in erythromycin production compared to the parent control strain were characterized further in shake flask fermentations. Ery-up mutants that were derived by single crossover insertion were subjected to a plasmid eviction procedure to isolate the gene replacement strain. Both the single crossover and gene replacement strains were tested in microfermentation and shake flask fermentation for reproducibility. After retesting 7 of the Ery-up mutants maintained a level of production consistantly greater than 50% above the parent control. The highest producing strain in microfermentation was 8.1-C3 (ave. 447 µg/ml, N=24), which represented a 101% increase over the parent strain (ave. 221 µg/ml, N=192). Sequence analysis of the rescued DNA revealed that the insert disrupted the 5' end of a gene with significant homology to the alpha subunit (MutB) of methylmalonyl CoA mutase (MCM) from a variety of species. The highest BLASTX match was to the alpha subunit of the MCM of *Streptomyces avermitilis* (E value $1e^{-86}$), showing nearly end to end identity over 2124 bp. Mutant 8.2-F1 showed a 64% increase in erythromycin production followed by 8.6-E8, which showed a 56% increase. Sequence analysis revealed that these mutants also contained insertions in the mutB gene Mutants 3.1-D5, 4.2-B3, 5.9-B9 and 8.1-A11 averaged 104% above the parent strain. The insertion occurred in the same location in the 3 mutants, although in opposite orientations, 238 bp within an ORF with significant sequence identity to cob(I) alamin adenosyltransferases (cob) from a variety of species. Using the forward and reverse transposon primers the entire adenosyltrasferase reading frame was sequenced and was found to be 612 bp long, based on direct comparison of the amino acid sequence of cobA homologs (i.e., E value $1e^{-77}$ compared to the *S. coelicolor* cobA homolog, cobO) and a 71% overall identity to the cobA gene of *Mycobacterium tuberculosis*. The cobA sequence potentially contains a good ribosome binding site (GGGAGG) 7 bp upstream from the predicted start site, but translational coupling to the upstream chelatase gene cannot be ruled out. The ORF would encode a protein of almost 23 Kda. CobA is involved in the adenosylation of vitamin $B_{12}$ to form the active coenzyme $AdoB_{12}$ in both de novo biosynthesis and of adenosylation of exogenous corrinoids. CobA is a highly conserved protein throughout nature. Starting 8 bp downstream from the stop codon of cobA and extending 521 bp in the same transcriptional orientation another ORF involved in vitamin $B_{12}$ biosynthesis was identified. The ORF, presently consisting of a little more than a quarter of the predicted full-length DNA sequence, showed significant sequence identity to cobB, which encodes a cobyrinic acid a,c diamide synthase. The best BLASTX match was to the *S. coelicolor* cobB (E value $5.8 e^{-50}$). Using the transposon reverse primer to obtain sequences upstream of cobA identified another partial ORF involved in vitamin $B_{12}$ biosynthesis. Spanning 171 bp the *A. erythreum* ORF showed significant sequence identity to a putative chelatase of *S. coelicolor* (E value $1.5 e^{-7}$). Vitamin $B_{12}$ chelatases are involved in the insertion of a cobalt atom into the corrin ring and have been well characterized in other bacterial systems.

Fifteen Ery-down mutants were obtained in the initial microfermentation screen. Seven of these mutants were determined to be gene replacements and were retested in microfermentations and in shake flasks. The range of erythromycin production was between 3 µg/ml (1.6-B11) and 40 µg/ml (8.1-A11). Shake flask fermentations of the Ery-down mutants showed that the low producing phenotype was maintained when scaled up with and without soybean oil supplementation, indicating that the decrease in erythromycin production was not due to a defect in oil utilization. Sequence analysis of 7 retrieved plasmids revealed that 4 of the Ery-down mutants contained inserts within ero cluster genes. Mutant 1.6-B 11 contained an insertion 289 bp into eroCIII, a desosaminyltransferase which attaches the amino sugar desosamine to the polyketide backbone. Thin layer chomatography showed that mutant 1.6-B11 produced mainly α-mycarosyl-erythronolide B (MEB), as would be expected for an eryC mutant, but somewhat unexpectedly also produced a bioactivity level of erythromycin A (ErA) corresponding to an average of 13 µg/ml (N=6). This suggests that there may be another desosaminyltransferase in this organism, albeit with lower activity than eroCIII. Mutant 3.1-A3 contained an insertion 588 bp into eroBIII, an eryB gene with methyltransferase activity. Thin layer chomatography showed that this mutant made low levels of ErA, erythromycin C (ErC) and erythronolide B (EB) with bioactivity corresponding to an average of 5 µg/ml (N=6). In *S. erythraea* eryBIII mutants accumulate EB, so the presence of ErA and ErC in the fermentation broths suggested that there is another methyltransferase functional in *A. erythreum* erythromycin production, since the gene is predicted to be knocked out. This enzyme would be significantly less active than eryBIII, since the bioactivity levels of the ErA and ErC produced were about 2% of the parent. Mutant 3.1-E3 contained an insertion 148 bp into eroF. Thin layer chomatography revealed that mutant 3.1-E3 made lower levels of ErA only. This suggests that there is another C-6 hydroxylase, although with lower activity than eroF, since the insertion would be expected to knock out gene function. The last ero cluster mutant, 5.6-A3, contained an insertion in eroBIV, the mycarosyltransferase gene. The three other Ery-down mutants had insertions located outside of the cluster. Mutant 1.8-F5 contained an insertion within a gene with significant homology to Cytochrome B reductases of the Cytochrome bc complex from many species. The *A. erythreum* gene had 59% identity over 309 amino acids in the N-terminal portion to the QcrB and QcrB2 proteins of *S. coelicolor*, respectively (E value $1.1 e^{-47}$ and $3.6 e^{-46}$). These proteins are involved in forming the Cytochrome bc reductase complex. Immediately downstream of the QcrB homolog another ORF with significant identity to the *A. erythreum* sequences was identified, encoding a gene in the rpiR family of transcriptional regulators (E value $2 e^{-13}$). At present it is not known which gene(s) have been affected to give the erythromycin phenotype, since it is possible that one or both could play a role in decreasing antibiotic production. Mutant 1.8-F7 had marginal (41%; E value $1e^{-3}$) sequence identity over 213 amino acids to NifA, a positive regulator of nitrogen fixation genes in the plant root symbiont *Azospirillium brasilense*. Further analysis of this mutant is underway to determine the gene(s) involved in the Ery-down phenotype. Mutant 8.1-A11 contained an within a methionine aminopeptidase (map') homolog. The best BLASTX match was to the map gene of *Bifidobacterium longum* NCC2705 (E value $1e^{-67}$).

Plasmids rescued from 3 null mutants determined by bioassay were analyzed by BLASTX searches and thin layer chromotography. One of the mutants contained an insertion in an ero cluster gene, whereas 2 contained insertions outside the erythromycin biosynthetic genes. Mutant strain 1.7-H4 had a null phenotype that was derived by single crossover insertion, since the transposon was determined to have inserted into the plasmid backbone. Sequencing using the forward primer revealed only plasmid sequences. Sequencing using the reverse primer revealed that the transposon had inserted near a neutral site upstream of the ColE1 origin, 380 bp from the BamHI site of the polylinker. Sequencing beyond the BamHI site allowed the identification of 439 bp into the cloned *A. erythreum* DNA. BLASTX analysis revealed significant identity to SocE (E value $1e^{-20}$), a *Myxococcus xanthus* gene encoding a negative regulator of the stringent response. This gene could potentially be involved in a regulatory cascade that affects erythromycin production, and is undergoing further analysis by generation of a gene replacement strain. Mutant strain 1.2-H10 is a null mutant also derived by single crossover insertion. BLASTX analysis did not reveal any significant matches in the region affected by the insertion of the transposon. Located 297 bp downstream from the insertion site and spanning 488 bp was a region showing significant sequence identity (62%) to a putative secreted protein of *S. coelicolor* (E value $2.7\ e^{-47}$). This mutant is also undergoing further analysis by the generation of a gene replacement strain. Sequence analysis of mutant 1.6-F7 rescued DNA revealed that the transposon had inserted into module 4 of the eroAIII gene, which is involved in the biosynthesis of the polyketide backbone. A single crossover insertion into eroAIII would be predicted to exert a polar effect on the downstream polyketide synthase modules resulting in a null phenotype.

To test if a chemical analysis of the culture broths from these null mutants would be consistant with the bioassay data thin layer chromotography was performed on extracts from 5-day shake flask fermentation cultures. The results showed that no erythromycin intermediates or ErA was produced in any of the mutants.

Gene for Methylmalonyl-CoA Mutase and Gene for cobA

In another aspect, the present invention provides isolated and purified genes that encode wild-type and mutant forms of Methylmalonyl-CoA Mutase (MCM) and cobA.

In another aspect, the present invention provides an isolated and purified mutant Methylmalonyl-CoA Mutase (MCM) gene that encodes an inactive form of the enzyme. FIG. 2 shows a partial nucleotide sequence of wild type MCM mutB gene from *Aeromicrobium erythreum*. In FIG. 2, the bolded base pairs indicate the point of transposon insertion for mutating the wild-type MCM gene. FIG. 3 shows the nucleotide sequence of the modified EZ:TN<TET> transposon used to generate the mutB and cobA mutations. The mutant mutB gene of the subject invention thus has a transposon insertion (transposon size 3,764 bp) approximately midway within the mutB gene such that the gene has been rendered non-functional. In addition, the mutB mutant contains a 9-bp duplicated sequence on both sides of the transposon site. This is standard for insertion mutations using Tn5-based transposons.

As mentioned above, FIG. 3 shows the nucleotide sequence of the modified EZ:TN<TET> transposon used to generate the mutB and cobA mutations. It contains the 19-bp repeats for Tn5 recognition, a thiostrepton-resistance gene (tsr) for selection in *Aeromicrobium erythreum*, a tetracycline gene (tet) for selection in *E. coli*, the conditional origin of replication R6Kγ, used for the recovery of the transposon in *E. coli*, and permE*, used for overexpression of genes located downstream of the transposon insertion.

FIG. 4 shows the nucleotide sequence of wild-type cobA, a cob(I)alamin adenosyltransferase involved in the biosynthesis of coenzyme $B_{12}$ or the conversion of exogenous vitamin $B_{12}$ to its active form, coenzyme $B_{12}$. In FIG. 4, the bolded base pairs indicate the point of transposon insertion for mutating the wild-type cobA gene. The mutant cobA gene of the subject invention thus has a transposon insertion 238 bp into the coding sequence such that the gene has been rendered non-functional. As found in the mutB mutant the cobA mutant contains the entire 3,764 bp transposon as well as the 9 bp duplicated Tn5 recognition sequences.

The present invention further provides expression vectors containing such wild-type and mutated genes and host cells transformed with such expression vectors. As is well known in the art, particular expression vectors are particularly suitable for particular cell types.

The Examples that follow illustrate preferred embodiments of the present invention and are not limiting of the specification and claims in any way.

EXAMPLES

Fermentations. Screening of the *A. erythreum* mutant library was performed in 96-deep-well poly propylene microtiter plate (fermentations that were set on top of the model 710022 rotary tumble stirrer (V& P Scientific, Inc., San Diego, Calif.). Each well contained 500 µl of 2×YTG (0.4% or 1.5% glucose) or SCM medium (Paulus et al., 1990) containing glucose (1.5%), vitamins and trace elements (Kieser et al., 2000). Cultures were stirred with 31.8 mm long by 1.58 mm diameter stainless steel Stir StiX (V& P Scientific, Inc.) provided by the manufacturer. *A. erythreum* Tn mutants were directly inoculated into wells from the transformation plate or from patches on antibiotic plates using a sterile Stir StiX and forceps. Cultures were stirred at a power setting of 2 (equal to 20% output). The entire rotary tumble stirrer was maintained inside a Labline shaker/incubator to control temperature and humidity. To generate master stock cultures for permanent storage of insertion mutants, cultures were incubated at 32° C. for 36 hours and mixed with an equal volume of 40% glycerol. These master stock cultures (200 µl/well) were stored in shallow well microtiter dishes and kept at −80° C. for later use. For microfermentations in which the erythromycin yield would be assayed, 10 µl of the glycerol stock culture was autopipetted (Matrix Technologies Corp., Hudson, N.H.) into 500 µl of fermentation medium and incubated at 32° C. for 72 hours. A cover consisting of the microtiter dish lid (VWR) with a sterile Kimwipe tissue was used to minimize well to well splashing and evaporation. Humidification was maintained between 40%-60% throughout the fermentation. Shake flask fermentations were performed as described previously (Reeves et al., 2002).

*A. erythreum* genomic library construction. An *A. erythreum* library was constructed from genomic Sau3A1 fragments in the 8-20 kb range. The Sau3A1 fragments were ligated to dephosphorylated, BamHI-digested pFL2082 a pUC19-derived vector containing the aph1 gene from Tn903 cloned into the SspI site. E. coli DH5α-e transformants were plated on SOB agar plates (Sambrook et al., 1989) containing kanamycin, ampicillin and X-gal. The ligations were optimized until a 10 to 1 ratio was obtained of white colonies containing inserts to blue colonies not containing inserts.

In vitro transposon mutagenesis. A derivative of transposon EZ:TN™<TET-1> (Epicentre Technologies, Madison, Wis.) was generated which contained tsr, a thiostrepton resistance gene from pIJ487 (Ward et al., 1986), the R6Kγ ori from EZ:TN™<R6Kγ-ori/Kan-2> (Epicentre) and the ermE* promoter described by Bibb et al., (1994). The transposon was constructed from a 1.7 kb Tn<TET-1> blunt fragment containing the tetracycline resistance gene (Tet$^r$) and from the 19 bp mosaic ends recognized by Tn5, cloned into the larger (2.3 kb) PvuII fragment of pUC19 to create pFL3010. Next, the tsr gene was created by PCR from pFL8 (Reeves et al., 2002) with an EcoRI site engineered at one 5' end and a KpnI site at the other 5' end. After EcoRI and KpnI digestion of the PCR product, the 1.0 kb tsr gene fragment was ligated to similarly digested pFL3010. The resulting construct was designated pFL3012.

pIJ4070 (Bibb et al., 1994) was digested with MscI and PstI, releasing a 280 bp fragment containing the ermE* promoter. The MscI/PstI fragment was ligated to similarly digested pFL3012 to yield pFL2083. Finally, the 800 bp R6K γ ori fragment from EZ:TN<R6Kγ ori/Kan-2> was amplified by PCR with EcoRI sites engineered at the ends. After EcoRI digestion the R6Kγ ori was ligated to similarly digested pFL2083 to yield pFL2087A and pFL2087B, depending on the orientation of the cloned fragment. For in vitro mutagenesis reactions linear transposon DNA was generated from pFL2087 by partially digesting with PvuII and gel purifying a 3.74 kb fragment. The in vitro transposon mutagenesis reaction was performed according to the manufacturer's instructions using a plasmid to transposon fragment ratio of 4 to 1. Following transformation of the transposon-mutagenized library in E. coli recombinant cells were selected on SOB agar diffusion plates (Fleischmann et al., 1995) containing tetracycline at 10 μg/ml, kanamycin at 50 μg/ml, ampicillin at 50 μg/ml and X-gal indicator. Selecting with all three antibiotics aided in eliminating some of the plasmids containing transposons which had inserted into the vector backbone.

Analysis of fermentation broths by bioassay. Analytical techniques. Erythromycin concentrations from microfermentations and shake flask fermentations of A. erythreum parent and Tn mutants were determined by bioassay. Thin-layer chromatography was performed to visualize the erythromycins and their intermediates produced in various Tn mutants and was performed as described previously by Weber et al., (1985) using either the large-scale technique (25 ml shake flask cultures) or the scaled-down (1 ml cultures) procedure.

Plasmid recovery and DNA sequence analysis of the transposon insertion site. Plasmid eviction and rescue. Tn mutants harboring transposon DNA along with vector DNA derived by single crossover insertion were cured of the plasmid portion by an eviction procedure that involved maintenance of the selectable thiostrepton marker located on the transposon. Mutants were grown in 2×YTG medium supplemented with thiostrepton at 5 μg/ml for 2 days. Aliquots (100 μl) of the turbid culture were plated on 2×YTG plates containing thiostrepton at 25 μg/ml and incubated at 32° C. for an additional 5 days. To identify mutants that have undergone eviction of the plasmid backbone (gene replacement), a 1' streak from the lawn of cells was resuspended in 1 ml of broth (cell density estimated to be about $10^8$/ml) and identical aliquots of dilutions ranging from $10^6$ to $10^8$ were spread onto 2×YTG plates supplemented with thiostrepton and kanamycin. This process was repeated until the ratio of Thio$^r$/Kn$^r$ colonies to Thio$^r$/Kn$^s$ colonies was about 2 to 1. Gene replacement candidates (Thio$^r$/Kn$^s$) were identified by replica patching individual colonies from the thiostrepton-supplemented plate onto fresh 2×YTG plates containing thiostrepton and kanamycin.

Plasmid rescue was performed on A. erythreum Tn mutants by purifying total chromosomal DNA and digesting with the frequent cutting restriction enzymes XhoI, BssHII, ApaI, StuI and MluI. None of these enzymes cuts within the transposon and therefore was used for retrieving Tn DNA and sequences adjacent to the insertion site. Following digestion, total restricted DNA was subjected to overnight ligation with T4 DNA ligase (Fermentas). The ligated DNA was transformed by electroporation into the pir$^+$-containing E. coli cell line EC100D-pir-116 (Epicentre Technologies) and plated on Luria Broth (LB) agar (Sambrook et al., 1989) plates supplemented with (Tet) at 10 μg/ml. Plasmid DNA from two to five Tetr colonies was analyzed by restriction digestion with the same enzyme used in the rescue procedure. Plasmids that showed a consistant restriction pattern were used for sequence analysis of the A. erythreum genomic DNA.

Sequencing genomic DNA adjacent to the transposon insertion site. DNA sequencing reactions were performed using the Big Dye Terminator Cycle Sequencing Kit (Applied Biosystems, Foster City, Calif.) according to the manufacturer's protocol. Cycled DNA was precipitated with ethanol and resolved at Davis Sequencing, LLC (Davis, Calif.). All sequences were analyzed by the NCBI BLAST program with default settings. The two sequencing primers used in all reactions were located at the ends of the modified transposon and were as follows: Forward Tn primer, (87tet-FP2), 5'-GCTGGACAATCGTGCCGGTT-3' (SEQ ID NO. 4), and Reverse Tn primer, (87tet-RV3), 5'-GGAACACCTACATCTGTATTAACG-3' (SEQ ID NO: 5).

Analysis of mutants that showed an increase in erythromycin yield. Approximately 54% (3,049/5,694) of the mutants from the 2 libraries, 2,267 from pools 1-5 of the initial library and all 782 mutants from the gene replacement library were screened in duplicate microfermentations for their erythromycin production. A total of 26 mutants were analyzed by BLASTX analysis of the retrieved gene or plasmid sequences disrupted by the insertion from strains exhibiting an altered erythromycin yield (Table 2). Of this total, 28 mutants (~1%) produced greater than 50% above the parent control strain and were analyzed further. These 28 mutants were grouped into single crossover mutants (3) and gene replacement mutants (25), hereafter designated Ery-up mutants. All the Ery-up mutants were subjected to microfermentations where the number of replicates ranged from N=24 to N=96. Strains that maintained a 50% increase in erythromycin production compared to the parent control strain were characterized further in shake flask fermentations. Ery-up mutants that were derived by single crossover insertion were subjected to a plasmid eviction procedure to isolate the gene replacement strain. Both the single crossover and gene replacement strains were tested in microfermentation and shake flask fermentation for reproducibility. After retesting 6 of the Ery-up mutants maintained a level of production consistantly greater than 50% above the parent control. The highest producing strain in microfermentation was 8.1-C3 (ave. 447 μg/ml, N=24), which represented a 101% increase over the parent strain (ave. 221 μg/ml, N=192). Sequence analysis of the rescued DNA revealed that the insert disrupted the 5' end of a gene with significant homology to the alpha subunit (MutB) of methylmalonyl CoA mutase (MCM) from a variety of species. The highest BLASTX match was to the alpha subunit of the MCM of *Streptomyces avermitilis* (E value 1e$^{-86}$), showing end to end identity over 1450 bp. Mutant 8.2-F1 showed a 64% increase in erythromycin production followed by 8.6-E8, which showed a 56% increase. Sequence analysis revealed that these mutants also contained insertions in the mutB gene . . . Mutants 3.1-D5 and 4.2-B3 averaged 104% above the parent strain. The insertion occurred in the same location in the 3 mutants, although in opposite orientations, 238 bp within an ORF with significant sequence identity to cob(I) alamin adenosyltransferases (cob) from a variety of species. Using the forward and reverse transposon primers the entire adenosyltrasferase reading frame was sequenced and was found to be 612 bp long, based on direct comparison of the amino acid sequence of cobA homologs (i.e., E value 1e$^{-77}$ compared to the *S. coelicolor* cobA homolog, cobO) and a 71% overall identity to the cobA gene of *Mycobacterium tuberculosis* (Table 2). The cobA sequence potentially contains a good ribosome binding site (GGGAGG) 7 bp upstream from the predicted start site, but translational coupling to the upstream chelatase gene cannot be ruled out The ORF would encode a protein of almost 23 Kda. CobA is involved in the adenosylation of vitamin $B_{12}$ to form the active coenzyme AdoB$_{12}$ in both de novo biosynthesis and of adenosylation of exogenous corrinoids (Refs). CobA is a highly conserved protein throughout nature and an alignment of the *A. erythreum* CobA homolog with other CobA proteins is shown in FIG. 5. Starting 8 bp downstream from the stop codon of cobA and extending 521 bp in the same transcriptional orientation another ORF involved in vitamin $B_{12}$ biosynthesis was identified. The ORF, presently consisting of a little more than a quarter of the predicted full-length DNA sequence, showed significant sequence identity to cobB, which encodes a cobyrinic acid a,c diamide synthase. The best BLASTX match was to the *S. coelicolor* cobB (E value 5.8 e$^{-50}$). Using the transposon reverse primer to obtain sequences upstream of cobA identified another partial ORF involved in vitamin $B_{12}$ biosynthesis. Spanning 171 bp the *A. erythreum* ORF showed significant sequence identity to a putative chelatase of *S. coelicolor* (E value 1.5 e$^{-7}$). Vitamin $B_{12}$ chelatases are involved in the insertion of a cobalt atom into the corrin ring and have been well characterized in other bacterial systems.

Protoplast transformations. *A. erythreum* B-3381 was transformed using a modified protoplast transformation procedure originally described by Roberts et al., (1987). *A. erythreum* was inoculated into culture tubes containing 4 ml of 2× YTG and incubated at 32° C. for 17-18 hours. The overnight culture was diluted 1:10 in 25 ml of the same medium and allowed to grow for another 2-4 hours at 32*C with shaking at 350 rpm. After the outgrowth period, cells were pelleted by room temperature centrifugation at 5000 rpm for 10 minutes followed by a wash in 20 ml of 0.3M sucrose. After pelleting, cells were resuspended in 5 ml of 1× P buffer (Rodicio and Chater, 1982; Kieser et al., 2000) containing 5 mg of lysozyme per ml. Protoplasting was performed at 32° C. for 2 hours. After incubation protoplasts were pelleted as before followed by a wash step in 20 ml of 1× P buffer. After a final pelleting step, protoplasts were resuspended in 1 ml of P buffer and either used immediately or stored at –80° C.

Transformations of Tn-mutagenized library DNA were performed according to a modified procedure described by Roberts et al., (1987) and Miller (1991). Two hundred microliter aliquots of protoplasts were pipetted into eppendorf tubes containing 26 µl of Qiagen-prepped DNA that had been previously alkaline-denatured according to the procedure described by Oh and Chater, 1997). The protoplast/DNA mixture was mixed gently by tapping the tube followed immediately by the addition of 800 µl of 2× P buffer containing 50% polyethylene glycol (mw (10,000). The mixture was vortexed 1-2 seconds to disperse the protoplasts. The entire protoplast mixture (ca. 1 ml) was spread evenly over an R2T2 plate that was dried to 95% of its original weight. The transformation plate was incubated at 32° C. for 22 hours. Thiostrepton-resistant transformants were selected by flooding the plate with 1 ml of a solution containing 800 µg of the antibiotic per ml. To improve growth of the transformants, agar layers were transferred (underlayed) after 3-5 days to 2×YTG agar plates containing thiostrepton at 25 µg/ml. Transformants were scored after 5-6 days at 32° C.

Protoplast transformations with denatured *A. erythreum* chromosomal DNA were performed according to the procedure described by Oh and Chater (1997) using type strain NRRL B-3381 as the recipient. Donor DNA (up to 10 µg) was derived from chromosomal preparations of Tn mutants and B-3381 recipients were selected with thiostrepton as described above. Gene replacement strains were confirmed by PCR of known sequences contained on the transposon and adjacent genomic DNA.

Bacterial strains and culture conditions. *A. erythreum* B-3381 was obtained from the Northern Regional Research Laboratory (Peoria, Ill.). Cells were routinely cultured on 2× YT agar (Sambrook et al., 1989) plates supplemented with 0.4% glucose (2×YTG) or grown overnight in 2×YTG broth or soluble complete medium (SCM; -Paulus et al., 1990), supplemented with trace elements (- Kieser et al., 2000) and 1.5% glucose. *E. coli* DH5α-e (Invitrogen, Carlsbad, Calif.) was grown in Luria Broth (Sambrook et al., 1989) and maintained on LB agar. When appropriate, *A. erythreum* agar and liquid cultures were supplemented with 5 µg/ml kanamycin sulfate and 10-50 µg/ml thiostrepton. *E. coli* media were supplemented with 10 µg/ml tetracycline (Tet) for selection and maintenance of the transposon cassette and 50 µg/ml kanamycin (Kn) and ampicillin (Ap) for selection and maintenance of recombinant plasmids.

Our procedure involved several modifications of the liquid and solid growth medium used to prepare the cells for protoplasting as well as protoplast regeneration after transformation. The liquid growth medium described by Roberts et al., (1987) was 1× YT+Mg and 0.5% glucose (8 g Tryptone, 5 g yeast extract, 2.5 g NaCl, 5 g glucose, and 1 g MgCl$_2$ per liter). We increased the nutrient content of the liquid growth medium to 2× YTG (1% glucose) without MgCl. We found that this medium increased the growth rate of cells so that a higher density of protoplasts was obtained from a similar volume of culture without affecting the transformation frequency. 2×YTG was also used with and without antibiotics as the solid medium for maintenance, screening of recombinants, and underlaying transformation plates instead of a 1× YT-based agar.

DNA manipulations. DNA manipulations including plasmid DNA isolation, restriction digestion, dephosphorylations with calf or shrimp alkaline phosphatase (Roche Molecular Biochemicals, Indianapolis, Ind.), 5' or 3' end-filling reactions with T4 DNA polymerase or Klenow large fragment polymerase (Roche Molecular Biochemicals), and ligations with T4 DNA ligase (Fermentas, Vilnius, Lithuania) were performed using standard procedures (Sambrook et al., 1989) or those outlined by the manufacturer. Plasmid DNA isolation for use in protoplast transformations of *A. erythreum* was purified using the Qiagen Midiprep Kit (Qiagen, Valencia, Calif.). For *E. coli* electroporations, DH5□e was used (Invitrogen Life Technologies, Carlsbad, Calif.). When using restriction enzymes inhibited by dam or dcm methylase, *E.* coli MCR-DH5α was used. For amplification reactions, a premixed 2× taq polymerase PCR mix containing 2 mM $Mg^{2+}$ (Fermentas) and 10% DMSO was used. For isolation of *A. erythreum* chromosomal DNA, 800 µl of a dense overnight culture was mixed with 250 µl of phenol:chloroform (Amresco, Solon Ohio), vortexed vigorously for 10 seconds, and centrifuged for 3 minutes at 15,000 rpm. The supernatant was reextracted with 250 µl of phenol:chloroform and centrifuged as before. The supernatant was precipitated with 0.6 volumes of isopropyl alcohol and ¹/₁₀ volume of ammonium acetate, pH 5.2. The chromosomal DNA was collected as a pellet after a 5 second centrifugation at 10,000 rpm. Southern blotting was performed as described previously (- Reeves et al., 2002

*A. erythreum* genomic library construction. A genomic library of total *A. erythreum* DNA was constructed by partially digesting 10 µg of chromosomal DNA with Sau3A1 so that the majority of the fragments were in the 8-20 kb range. After purification from a 0.6% agarose gel, the Sau3A1 fragments were ligated to dephosphorylated, BamHI-digested pFL2082 (Table 1), a pUC19-derived vector containing the aph1 gene from Tn903 cloned into the SspI site. The aph1 gene confers kanamycin resistance in both *E. coli* and *A. erythreum* (ref. Roberts et al). Ligation mixtures were transformed into *E. coli* DH5α-e by electroporation. Transformants were plated on SOB agar plates (Sambrook et al., 1989) containing kanamycin, ampicillin and the color indicator X-gal. Ligation reactions were performed until the ratio of white colonies to blue colonies was about 10.

Colorimetric plate assay to distinguish single crosses from double crosses. Distinguishing between *A. erythreum* Tn mutants derived by single, reciprical crossover insertion or double crossover insertion (gene replacement) on the transformation plate required the development of a simple, visual plate assay that took advantage of the kanamycin resistance gene located on the plasmid backbone. The main difference between the standard transformation procedure and the colorimetric plate assay was the addition of a second underlay step which involved transferring the top agar layer to fresh agar plates supplemented with kanamycin, thiostrepton and the vital dye 2,3,5-triphenyltetrazolium chloride (tetra red). Transformation plates were treated in exactly the same manner as described above, except that after 2 days of growth on the initial thiostrepton-only underlay plate the top agar layer was transferred to a fresh 2×YTG plate containing kanamycin at 20 µg/ml, thiostrepton at 25 µg/ml, and 2,3,5-triphenyltetrazolium chloride at a final concentration of 72 µM. Tn mutants were scored 40 hr post underlay on the basis of their kanamycin phenotype ($Kn^s$ vs. $Kn^r$), colony size, and colony color (dark red vs. orange).

Analytical techniques. Erythromycin concentrations from microfermentations and shake flask fermentations of *A. erythreum* parent and Tn mutants were determined by bioassay as described previously. Thin-layer chromatography was performed to visualize the erythromycins and their intermediates produced in various Tn mutants and was performed as described previously by Weber et al., (1985) using either the large-scale technique (25 ml shake flask cultures) or the scaled-down (1 ml cultures) procedure (Reeves et al, 2002).

REFERENCES

Aparicio J F, Caffiey P, Gil J A. Zotchev S B. Polyene antibiotic biosynthesis gene clusters. Appl Microbiol Biotechnol. 2003 May;61(3):179-88. Epub 2002 December 18.

Aparicio J F, Molnar I, Schwecke T. Konig A, Haydock S F, Khaw L E, Staunton J, Leadlay P F. Organization of the biosynthetic gene cluster for rapamycin in *Streptomyces hygroscopicus*: analysis of the enzymatic domains in the modular polyketide synthase. Gene. 1996 Feb. 22; 169(1): 9-16.

Bibb M J, White J. Ward J M, Janssen G R. The mRNA for the 23S rRNA methylase encoded by the ermE gene of *Saccharopolyspora erythraea* is translated in the absence of a conventional ribosome-binding site. Mol Microbiol. 1994 November;14(3):533-45.

Birch A, Leiser A, Robinson J A. Cloning, sequencing, and expression of the gene encoding methylmalonyl-coenzyme A mutase from *Streptomyces cinnamonensis*. J. Bacteriol. 1993 June;175(11):3511-9.

Dayem L C. Carney J R, Santi D V, Pfeifer B A, Khosla C, Kealey J T. Metabolic engineering of a methylmalonyl-CoA mutase-epimerase pathway for complex polyketide biosynthesis in *Escherichia coli*. Biochemistry. 2002 Apr. 23; 41(16):5193-201.

Donadio S, Staver M J, Katz L. Erythromycin production in *Saccharopolyspora erythraea* does not require a functional propionyl-CoA carboxylase. Mol Microbiol. 1996 March; 19(5):977-84.

Dotzlaf J E, Metzger L S, Foglesong M A. Incorporation of amino acid-derived carbon into tylactone by *Streptomyces fradiae* GS 14. Antimicrob Agents Chemother. 1984 February;25(2):216-20.

Fleischmann R D, Adams M D, White O, Clayton R A, Kirkness E F, Kerlavage A R, Bult C J, Tomb J F, Dougherty B A, Merrick J M, et al. Whole-genome random sequencing and assembly of *Haemophilus influenzae* Rd. Science. 1995 Jul. 28; 269(5223):496-512.

Gerth K, Bedorf N, Irschik H, Hofle G, Reichenbach H. The soraphens: a family of novel antifungal compounds from Sorangium cellulosum (Myxobacteria). I. Soraphen Al alpha: fermentation, isolation, biological properties. J Antibiot (Tokyo). 1994 January;47(1):23-31.

Gil J A. Campelo-Diez A B. Candicidin biosynthesis in *Streptomyces griseus*. Appl Microbiol Biotechnol. 2003 February;60(6):633-42. Epub 2002 December 18. Review.

Goryshin, I. Y., and W. S. Reznikoff. 1998. Tn5 in vitro transposition. J. Biol. Chem. 273: 7367-7374.

Haydock S F, Aparicio J F, Molnar I, Schwecke T, Khaw L E, Konig A, Marsden A F, Galloway I S, Staunton J. Leadlay P F. Divergent sequence motifs correlated with the substrate specificity of (methyl)malonyl-CoA:acyl carrier protein transacylase domains in modular polyketide synthases. FEBS Lett. 1995 Oct. 30; 374(2):246-8.

Hsieh Y J, Kolattukudy P E. Inhibition of erythromycin synthesis by disruption of malonyl-coenzyme A decarboxylase gene eryM in *Saccharopolyspora erythraea*. J. Bacteriol. 1994 February;176(3):714-24.

Hunaiti A A, Kolattukudy P E. Source of methylmalonyl-coenzyme A for erythromycin synthesis: methylmalonyl-coenzyme A mutase from *Streptomyces erythreus*. Antimicrob Agents Chemother. 1984 February;25(2):173-8.

Hu Z, Bao K. Zhou X, Zhou Q, Hopwood D A, Kieser T. Deng Z. Repeated polyketide synthase modules involved in the biosynthesis of a heptaene macrolide by *Streptomyces* sp. FR-008. Mol Microbiol. 1994 October;14(1):163-72.

Ikeda H, Nonomiya T, Usami M. Ohta T. Omura S. Organization of the biosynthetic gene cluster for the polyketide anthelmintic macrolide avermectin in *Streptomyces avermitilis*. Proc Natl Acad Sci USA. 1999 Aug. 17; 96(17): 9509-14.

Keiser, T., Bibb, M. J., Buttner, M. J., Chater, K. F. & Hopwood, D. A. Practical *Streptomyces* Genetics (John Innes Foundation, Norwich, 2000.

Kellermeyer R W, Allen S H G, Stjernholm R, and Wood H G. Methylmalonyl isomerase. IV. Purification and properties of the enzyme from *Propionibacteria*. J. Biol. Chem. 1964 239: 2562-2569

Liu H, Reynolds K A. Role of crotonyl coenzyme A reductase in determining the ratio of polyketides monensin A and monensin B produced by *Streptomyces cinnamonensis*. J. Bacteriol. 1999 November;181(21):6806-13.

Marsh E N, McKie N, Davis N K, Leadlay P F. Cloning and structural characterization of the genes coding for adenosylcobalamin-dependent methylmalonyl-CoA mutase from *Propionibacterium shermanii*. Biochem J. 1989 Jun. 1; 260(2):345-52.

Mateles, Richard I. Penicillin: A Paradigni for Biotechnology Candida Corporation, Ill., ISBN 1 891545 01 9

Miller E S. Cloning vectors, mutagenesis, and gene disruption (ermR) for the erythromycin-producing bacterium *Aeromicrobium erythreum*. Appi Environ Microbiol. 1991 September;57(9):2758-61

Mochizuki S. Hiratsu K, Suwa M. ishii T. Sugino F. Yamada K. Kinashi H. The large linear plasmid pSLA2-L of *Streptomyces rochei* has an unusually condensed gene organization for secondary metabolism. Mol Microbiol. 2003 June;48(6):1501-10.

Molnar 1, Aparicio J F, Haydock S F, Khaw L E, Schwecke T, Konig A, Staunton J. Leadlay P F. Organisation of the biosynthetic gene cluster for rapamycin in *Streptomyces hygroscopicus*: analysis of genes flanking the polyketide synthase. Gene. 1996 Feb. 22; 169(1):1-7.

Oh S H, Chater K F. Denaturation of circular or linear DNA facilitates targeted integrative transformation of *Streptomyces coelicolor* A3(2): possible relevance to other organisms. J. Bacteriol. 1997 January;179(1):122-7.

Omura S, Tsuzuki K, Tanaka Y, Sakakibara H, Aizawa M, Lukacs G. Valine as a precursor of n-butyrate unit in the biosynthesis of macrolide aglycone. J Antibiot (Tokyo). 1983 May;36(5):614-6.

Omura S, Taki A, Matsuda K, Tanaka Y. Ammonium ions suppress the amino acid metabolism involved in the biosynthesis of protylonolide in a mutant of *Streptomyces fradiae*. J Antibiot (Tokyo). 1984 November;37(11):1362-9.

Omura, S., Macrolide Antibiotics: Chemistry, Biology, Practice, Aca-demic Press, New York, 1984.

Omura S, Takeshima H. Nakagawa A. Miyazawa J, Piriou F, Lukacs G. Studies on the biosynthesis of 16-membered macrolide antibiotics using carbon-13 nuclear magnetic resonance spectroscopy. Biochemistry. 1977 Jun. 28; 16(13):2860-6.

Paulus T J, Tuan J S, Luebke V E, Maine G T, DeWitt J P, Katz L. Mutation and cloning of eryG, the structural gene for erythromycin O-methyltransferase from *Saccharopolyspora erythraea*, and expression of eryG in *Escherichia coli*. J Bacteriol. 1990 May;172(5):2541-6.

Reeves A R, Weber G, Cemota W H, Weber J M. Analysis of an 8.1-kb DNA fragment contiguous with the erythromycin gene cluster of *Saccharopolyspora erythraea* in the eryCI-flanking region. Antimicrob Agents Chemother. 2002 December;46(12):3892-9.

Rodicio M R, Chater K F. Small DNA-free liposomes stimulate transfection of *streptomyces* protoplasts. J Bacteriol. 1982 September;151(3):1078-85.

Robelts A N, Barnett L, Brenner S. Transformation of *Arthrobacter* and studies on the transcription of the *Arthrobacter* ermA gene in *Streptomyces lividans* and *Escherichia coli*. Biochem J. 1987 Apr. 15; 243(2):431-6.

Rodriguez L. Aguirrezabalaga I. Allende N. Brana A F, Mendez C. Salas J A. Engineering deoxysugar biosynthetic pathways from antibiotic-producing microorganisms. A tool to produce novel glycosylated bioactive compounds. Chem Biol. 2002 June;9(6):721-9.

Sambrook, J., Fritsch, E. F., and Maniatis, T., (1989) "Molecular Cloning", Cold Spring Harbour Laboratory Press, ISBN 0-87969-309-6.

Schwecke T. Aparicio J F, Molnar 1. Konig A. Khaw L E, Haydock S F, Oliynyk M, Caffrey P, Cortes J, Lester J B, et al. The biosynthetic gene cluster for the polyketide immunosuppressant rapamycin. Proc Natl Acad Sci USA. 1995 Aug. 15; 92(17):7839-43.

Smith D B, Johnson K S. Single-step purification of polypeptides expressed in *Escherichia coli* as fusions with glutathione S-transferase. Gene. 1988 Jul. 15; 67(1):31-40.

Tang L, Zhang Y X, Hutchinson C R. Amino acid catabolism and antibiotic synthesis: valine is a source of precursors for macrolide biosynthesis in *Streptomyces ambofaciens* and *Streptomyces fradiae*. J Bacteriol. 1994 October;176(19): 6107-19.

Vlasie M D, Banerjee R. Tyrosine 89 accelerates Co-carbon bond homolysis in methylmalonyl-CoA mutase. J Am Chem Soc. 2003 May 7; 125(18):5431-5.

Ward J M, Janssen G R, Kieser T, Bibb M J, Buttner M J, Bibb M J. Construction and characterisation of a series of multicopy promoter-probe plasmid vectors for *Streptomyces* using the aminoglycoside phosphotransferase gene from Tn5 as indicator. Mol Gen Genet. 1986 June;203(3):468-78.

Weber J M, Wierman C K, Hutchinson C R. Genetic analysis of erythromycin production in *Streptomyces erythreus*. J Bacteriol. 1985 October;164(1):425-33.

Weber J M, Leung J O, Maine G T, Potenz R H, Paulus T J, DeWitt JP. Organization of a cluster of erythromycin genes in *Saccharopolyspora erythraea*. J Bacteriol. 1990 May; 172(5):2372-83.

Weber J M, Leung J O, Swanson S J, Idler K B, McAlpine JB. An erythromycin derivative produced by targeted gene disruption in *Saccharopolyspora erythraea*. Science. 1991 Apr. 5; 252(5002):114-7.

Wu K, Chung L, Revill W P, Katz L, Reeves C D. The FK520 gene cluster of *Streptomyces hygroscopicus* var. *ascomyceticus* (ATCC 14891) contains genes for biosynthesis of unusual polyketide extender units. Gene. 2000 Jun. 13; 251(1):81-90.

Xue Y. Wilson D, Sherman D H. Genetic architecture of the polyketide synthases for methymycin and pikromycin series macrolides. Gene. 2000 Mar. 7; 245(1):203-11.

Watson et al. *Molecular Biology of the Gene*, 4th Edition, 1987, The Bejacmin/Cummings Pub. co., p. 224).

Zhang W, Yang L, Jiang W, Zhao G, Yang Y, Chiao J. Molecular analysis and heterologous expression of the gene encoding methylmalonyl-coenzyme A mutase from rifamycin SV-producing strain *Amycolatopsis mediterranei* U32. Appl Biochem Biotechnol. 1999 December;82(3): 209-25.

From the foregoing, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

What is claimed is:

1. A method of increasing the production of an biologically active compound in an *Aeromicrobium erythreum* cell wherein the biologically active compound is derived from (2S)-methylmalonyl-CoA, the method comprising the step of inhibiting transcription of the cob(1)alamin adenosyltransferase gene by insertional mutagenesis in the cob(1)alamin adenosyltransferase gene in an *Aeromicrobium erythreum* cell;

wherein the biologically active compound is selected from the group consisting of an immunosuppressant, an anti-fungal agent, an anti-parasitic agent, an antibiotic, and an animal feed promotant; and wherein the production of the biologically active compound is increased when compared to production of the same biologically active compound by a corresponding cell wherein the activity of methylmalonyl-CoA mutase is not inhibited.

2. The method of claim 1 wherein the antibiotic is a polyketide antibiotic.

3. The method of claim 2 wherein the polyketide antibiotic is a macrolide polyketide antibiotic.

4. The method of claim 3 wherein the macrolide polyketide antibiotic is erythromycin, tylosin, niddamycin, spiramycin, oleandomycin, methymycin, neomethymycin, narbomycin, pikromycin, or lankamycin.

5. The method of claim 1 wherein the biologically active compound is an antibiotic.

* * * * *

UNITED STATES PATENT AND TRADEMARK OFFICE
CERTIFICATE OF CORRECTION

PATENT NO. : 7,638,306 B2
APPLICATION NO. : 10/637159
DATED : December 29, 2009
INVENTOR(S) : Weber et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1457 days.

Signed and Sealed this

Ninth Day of November, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 2124
<212> TYPE: DNA
<213> ORGANISM: Aeromicrobium erythreum

<400> SEQUENCE: 1

```
gcggtcgacg gcgccgagcc gtgggacgcc cccgagggca tcgcggtcaa gaacctctac      60
accgccgacg acctcgccga cgtcgacgcg ctcgacacct acccgggcct cgcgccgttc     120
ctgcgcggtc cctacccggc catgtacacg acccagccgt ggacgatccg ccagtacgcc     180
gggttctcga ccgccgagga gtcgaacgcg ttctaccgcc gcaacctcgc cgccggccaa     240
aagggcctct cggtcgcctt cgacctcgcg acgcaccgcg gctacgactc cgaccacccg     300
cgcgtgaagg gcgacgtcgg catggccggc gtcgcgatcg actcgatcta cgacgcccgc     360
cagctcttcg acggcatccc gctcgacgag atgagcgtct cgatgaccat gaacggcgcg     420
gtgctcccgg tgctcgcgct ctacatcgtg gcggccgagg agcaggggt gacgccggag     480
cagctctcgg ggaccatcca gaacgacatc ctcaaggagt tcatggtccg caacacctac     540
atctacccgc cggcgccgtc gatgcggatc atctccgaca tcttcgcgta cggcggcg      600
aagatgccgc ggttcaactc catctccatc tccgggtacc acatccaaga ggccggggcg     660
acgaacgacc tcgagctcgc ctacacgctc gccgacggtg tggagtacat ccgcgccggg     720
ctcgacgtcg gcctcgacat cgacgcgttc gcgccgcggc tcagcttctt ctgggccatc     780
ggcatgaact tctacatgga gatcgcgaag atgcgcgccg cccgtgccct gwgggcccgg     840
ctcgtgcgcg acttcgaccc gaagaacccc aagagcctca gcctgcgcac gcacagccag     900
acatcgggct ggagcctcac cgcgcaggac gtgttcaaca acgtccagcg cacctgcatc     960
gaggcgatgg ccgccacgca gggccacacc cagagcctgc acacgaacgc gctcgacgag    1020
gcgatcgcgc tgccgacgga cttcagcgcg cggatcgccc gcaacacgca gctgctgctg    1080
cagcaggagt cgggcaccac cggcgtcatc gacccgtggg gcggctccta ctacgtcgag    1140
aagctgacgc acgacctcgc gaaccgcgcc tgggcgcaca tccaggaggt cgagaaggcc    1200
ggcggcatgg ccaaggccat cgaggcgggc atccccaaga tgcgcgtcga ggaggcggcc    1260
gcccgcacgc aggcacgcat cgactccggc cagcaggccg tcatcggcgt caacacctac    1320
cgcctcgccg acgaggaccc gctcgacgtg ctcaaggtcg acaacgcgtc ggtctacgcc    1380
cagcaggtgg cgaagctcga gcgactgcgc gccgagcgcg acccgcagga ggtcgagcgc    1440
gcgctcgacg ccctgacggc cagcgccgag cgtggcgcca gccgcgacgg ctcgctcgac    1500
ggcaacctgc tcgccctggc cgtcgacgcg gcccgcgcga aggcgacggt cggcgagatc    1560
tcctacgcgc tcgagaaggt ctacgggcgc accaggccg tcatccgtac gatctccggt    1620
gtgtaccgga ccgaggcggg ccagggcggc aacgtccaga aggtcatcga cgccaccgag    1680
gcgttcgaga aggccgaggg tcgacgcccg cgcatcctcg tggccaagat gggccaggac    1740
ggccacgacc gcggccagaa ggtcatcgtc acggcgttcg ccgacatggg cttcgacgtc    1800
gacgtcggac cgctgttctc cacgcccgag gaggtcgcgc agcaggccgt ggacgccgac    1860
gtgcacatcg tcggcgtctc gagcctcgcg gcgggccacc tgacgctcct gccggagctg    1920
aagaaggcgt tggccgagct cggcggcgag gacgtcatgg tcgtcatggg tggcgtcatc    1980
ccgcccgacg acgtgccgac gctgaaggag atgggcgctg ccgaggtgtt cctgcccggc    2040
```

```
acggtcatcg ccgactccgc gctcagcctg ctcgagcggt ccgcgcgagc ctgcagcact    2100
agatggtcgg ttcgtccgag gtaa                                          2124

<210> SEQ ID NO 2
<211> LENGTH: 3764
<212> TYPE: DNA
<213> ORGANISM: Aeromicrobium erythreum

<400> SEQUENCE: 2
ctgtctctta tacacatctc aaccatcatc gatgaattcc accctgtgaa tgcgcaaacc      60
aacccttggc agaacatatc catcgcgtcc gccatctcca gcagccgcac gcggcgcatc     120
tcgggcagcg ttgggtcctg gccacgggtg cgcatgatcg tgctcctgtc gttgaggacc     180
cggctaggct ggcggggttg ccttactggt tagcagaatg aatcaccgat acgcgagcga     240
acgtgaagcg actgctgctg caaaacgtct gcgacctgag caacaacatg aatggtcttc     300
ggtttccgtg tttcgtaaag tctggaaacg cggaagtcag cgccctgcac cattatgttc     360
cggatctatg tcgggtgcgg agaaagaggt aatgaaatgg cagatccctg gcttgttgtc     420
cacaaccgtt aaaccttaaa agcttttaaaa gccttatata ttcttttttt tcttataaaa     480
cttaaaacct tagaggctat ttaagttgct gatttatatt aattttattg ttcaaacatg     540
agagcttagt acgtgaaaca tgagagctta gtacgttagc catgagagct tagtacgtta     600
gccatgaggg tttagttcgt taaacatgag agcttagtac gttaaacatg agagcttagt     660
acgtgaaaca tgagagctta gtacgtacta tcaacaggtt gaactgctga tcttcggatc     720
tatgtcgggt gcggagaaag aggtaatgaa atggcatccg gatctgcatc gcaggatgct     780
gctggctacc ctgtggaaca cctacatctg tattaacgaa gcaattcgaa ttcacagagg     840
cgcttatcgg ttggccgcga gattcctgtc gatcctctcg tgcagcgcga ttccgaggga     900
aacgaaaacg ttgagagact cggtctggct catcatgggg atggaaaccg aggcggaaga     960
cgcctcctcg aacaggtcgg aaggcccacc cttttcgctg ccgaacagca aggccagccg    1020
atccggattg tccccgagtt ccttcacgga aatgtcgcca tccgccttga gcgtcatcag    1080
ctgcataccg ctgtcccgaa tgaaggcgat ggcctcctcg cgaccggaga gaacgacggg    1140
aagggagaag acgtaacctc ggctggccct ttggagacgc cggtccgcga tgctggtgat    1200
gtcactgtcg accaggatga tccccgacgc tccgagcgcg agcgacgtgc gtactatcgc    1260
gccgatgttc ccgacgatct tcaccccgtc gagaacgacg acgtcccac gccggctcgc    1320 gatatcgccg aacctggccg ggcgagggac gcggcgatg ccgaatgtct tggccttccg    1380 ctccccttg aacaactggt tgacgatcga ggagtcgatg aggcggaccg gtatgttctg    1440
ccgcccgcac agatccagca actcagatgg aaaaggactg ctgtcgctgc cgtagacctc    1500
gatgaactcc accccggccg cgatgctgtg catgaggggc tcgacgtcct cgatcaacgt    1560
tgtctttatg ttggatcgcg acggcttggt gacatcgatg atccgctgca ccgcgggatc    1620
ggacggattt gcgatggtgt ccaactcagt catggtcgtc ctaccggctg ctgtgttcag    1680
tgacgcgatt cctggggtgt gacaccctac gcgacgatgg cggatggctg ccctgaccgg    1740
caatcaccaa cgcaagggga agtcgtcgct ctctggcaaa gctccccgct cttccccgtc    1800
cgggacccgc gcggtcgatc cccgcatatg aagtattcgc cttgatcaga tcaggtaccc    1860
ggggatcatc ttattaatca gataaaatat ttctagattt cagtgcaatt tatctcttca    1920
aatgtagcac ctgaagtcag ccccatacga tataagttgt aattctcatg tttgacagct    1980
```

```
tatcatcgat aagctttaat gcggtagttt atcacagtta aattgctaac gcagtcaggc    2040
accgtgtatg aaatctaaca atgcgctcat cgtcatcctc ggcaccgtca ccctggatgc    2100
tgtaggcata ggcttggtta tgccggtact gccgggcctc ttgcgggata tcgtccattc    2160
cgacagcatc gccagtcact atggcgtgct gctagcgcta tatgcgttga tgcaatttct    2220
atgcgcaccc gttctcggag cactgtccga ccgctttggc cgccgccag tcctgctcgc     2280 ttcgctactt ggagccacta tcgactacgc gatcatggcg accacacccg tcctgtggat    2340
cctctacgcc ggacgcatcg tggccggcat caccggcgcc acaggtgcgg ttgctggcgc    2400
ctatatcgcc gacatcaccg atggggaaga tcgggctcgc cacttcgggc tcatgagcgc    2460
ttgtttcggc gtgggtatgg tggcaggccc cgtggccggg ggactgttgg gcgccatctc    2520
cttgcatgca ccattccttg cggcggcggt gctcaacggc ctcaacctac tactgggctg    2580
cttcctaatg caggagtcgc ataagggaga gcgtcgaccg atgcccttga gagccttcaa    2640
cccagtcagc tccttccggt gggcgcgggg catgactatc gtcgccgcac ttatgactgt    2700
cttctttatc atgcaactcg taggacaggt gccggcagcg ctctgggtca ttttcggcga    2760
ggaccgcttt cgctggagcg cgacgatgat cggcctgtcg cttgcggtat tcggaatctt    2820
gcacgccctc gctcaagcct tcgtcactgg tcccgccacc aaacgtttcg gcgagaagca    2880
ggccattatc gccggcatgg cggccgacgc gctgggctac gtcttgctgg cgttcgcgac    2940
gcgaggctgg atggccttcc ccattatgat tcttctcgct tccggcggca tcgggatgcc    3000
cgcgttgcag gccatgctgt ccaggcaggt agatgacgac catcagggac agcttcaagg    3060
atcgctcgcg gctcttacca gcctaacttc gatcattgga ccgctgatcg tcacggcgat    3120
ttatgccgcc tcggcgagca catggaacgg gttggcatgg attgtaggcg ccgccctata    3180
ccttgtctgc ctccccgcgt tgcgtcgcgg tgcatggagc cgggccacct cgacctgaat    3240
ggaagccggc ggcaccctcgc taacggattc accactccaa gaattggagc caatcaattc    3300
ttgcggagaa ctgtgaatgc gcaaaccaac ccttggcaga acatatccat cgcgtccgcc    3360
atctccagca gcgcacgcgg cgcatctcgg gcacgttggg tcctggaatt cgagctcggt    3420
accagcccga cccgagcacg cgccggcacg cctggtagat gtcggaccgg agttcgaggt    3480
acgcggcttg caggtccagg aaggggacgt ccatgcgagt gtccgttcga gtggcggctt    3540
gcgcccgatg ctagtcgccg ttgatcggcg atcgcaggtg cacgcggtcg atcttgacgg    3600
ctggcgagag gtgcgggagg atctgaccga cccggtccac acgtggcacc gcgatgctgt    3660
tgtgggctgg acaatcgtgc cggttggtag gatcctctag agtcgacgca tgcaagcttc    3720
tgcaggcatg caagcttcag ggttgagatg tgtataagag acag                    3764
```

<210> SEQ ID NO 3
<211> LENGTH: 615
<212> TYPE: DNA
<213> ORGANISM: Aeromicrobium erythreum

<400> SEQUENCE: 3

```
atgccccagg gccagccgct ggtcgtcccc gacgacggcc tcaccacccg ccagcgtcgc      60
aaccgtccgc tcgtcatggt ccacaccggg cccggcaagg ggaagtcgac cgccgcgttc    120
ggcctcgcca tgcgcgcctg gaaccagggc tggaaggtcg gcgtgttcca gttcgtgaag    180
tccgccaagt ggcgcgtcgg cgagcagagc gtgctcgagc acctgggccg cctgcacgag    240
accgagggcc tcggcgggcc cgtcgagtgg cacaagatgg gctcgggctg gtcgtggtcg    300
cgcaagtcgg gcaccgacga cgaccacgcc gtcgccgccg ccgagggctg gccgagatc    360
```

```
aagcgtcgcc tcgccaccga gacgcacgac ctctacgtgc tcgacgagtt cacctacccg    420
atgaagtggg gctgggtcga cgtcgacgac gtcgccgaca cgctcgcgtc gcgcccggc     480 cgccagcacg tggtgatcac cggccgcgac gccgccccc  ggctcctgga ggtcgccgac    540
ctcgtcaccg agatgacgaa ggtcaagcac cccatggacg tcggccagaa gggtcagcga    600
ggcatcgagt ggtga                                                    615
```